United States Patent [19]

Arnould et al.

[11] Patent Number: 5,232,918
[45] Date of Patent: * Aug. 3, 1993

[54] CEPHALOSPORIN DERIVATIVES

[75] Inventors: Jean C. Arnould, Cromotreuil; Dominique Boucherot, Rilly la Montagne, both of France; David H. Davies, Sutton, England; Frederick H. Jung, Rilly la Montagne, France; Colin J. Strawson, Congleton, England

[73] Assignees: Imperial Chemical Industries PLC, London, England; ICI Pharma, Cergy Cedex, France

[ * ] Notice: The portion of the term of this patent subsequent to Apr. 16, 2008 has been disclaimed.

[21] Appl. No.: 653,149

[22] Filed: Feb. 11, 1991

Related U.S. Application Data

[62] Division of Ser. No. 223,988, Jul. 25, 1988, Pat. No. 5,019,570.

[30] Foreign Application Priority Data

Jul. 23, 1987 [EP] European Pat. Off. ........... 87401718

[51] Int. Cl.$^5$ ................. C07D 501/36; A61K 31/545
[52] U.S. Cl. .................... 514/202; 514/201; 540/221; 540/222; 540/225
[58] Field of Search ............... 540/221, 222; 514/202, 514/201

[56] References Cited

U.S. PATENT DOCUMENTS

| | | | |
|---|---|---|---|
| 5,008,259 | 4/1991 | Siret et al. | 540/222 |
| 5,019,570 | 5/1991 | Arnould et al. | 540/222 |
| 5,055,462 | 10/1991 | Daves et al. | 540/222 |

Primary Examiner—Nicholas S. Rizzo
Attorney, Agent, or Firm—Cushman, Darby & Cushman

[57] ABSTRACT

Cephalosporin derivatives having a 3-position substituent of formula I are described:

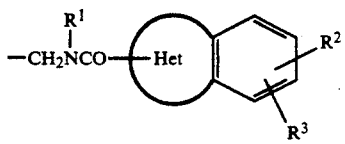

wherein $R^1$ is hydrogen, alkenyl or optionally substituted alkyl, Het is a 5- or 6-membered heterocyclic ring bonded via a carbon atom to the amide linkage, wherein Het is selected from a group of the formulae II-III:

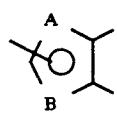

II

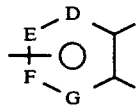

III wherein A is CH or a nitrogen atom; B is oxygen, sulphur or a group $NR^4$; one or two of D, E, F and G are nitrogen atoms and the remainder are CH groups: or Het is a pyrazinone, pyridinone, pyridazinone or pyrimidinone ring, or is a thione equivalent of such a ring, said rings having a substituent $R^4$ on one nitrogen atom, or is pyranone, or pyranthione; the ring Het being fused by any two adjacent carbon atoms to the benzene ring; and Het being attached to the —$CH_2NR^1CO$— group via a carbon atom;

$R^2$ is hydroxy or an in vivo hydrolysable ester thereof;
$R^3$ is ortho to $R^2$ and is hydroxy or an in vivo hydrolysable ester thereof; and $R^4$ has various values. The use of such compounds as antibacterial agents is described as are processes for their preparation and intermediates therefor.

8 Claims, No Drawings

CEPHALOSPORIN DERIVATIVES

This is a division of U.S. application Ser. No. 07/223,988, filed Jul. 25, 1988, now 5,019,570.

The present invention relates to cephalosporins and in particular to such compounds comprising an amide group. This invention further relates to processes for their preparation, to intermediates in their preparation, to their use as therapeutic agents and to pharmaceutical compositions containing them. The compounds of this invention are antibiotics and can be used in the treatment of any disease that is treated with antibiotics for example in the treatment of bacterial infection in animals, in particular in mammals including humans. The compounds of this invention also have non-therapeutic uses as they can be used in conventional manner in industry as is known to those in the art. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas including Ps. aeruginosa. The present invention provides cephalosporin derivatives having novel 3-position substituents, which derivatives possess good antibacterial activity against a wide range of organisms and show good stability to β-lactamases. These compounds are particularly advantageous in that they have excellent activity against strains of Ps. aeruginosa.

GB-B-2089339 and GB-B-2148282 discloses compounds wherein the 3-position substituent of a cephalosporin is of the formula: —CH$_2$R$^2$ wherein R$^2$ is a substituted or unsubstituted aryl, acylamino, aromatic heterocyclic, triazolyl or tetrazolyl group. In the above mentioned references the substituent "acyl" is able to have a variety of meanings but there is no teaching or suggestion of the compounds of the present invention which comprise specific ring systems having hydroxy groups or related substituents ortho to one another.

Accordingly the present invention provides a cephalosporin compound having a 3-position substituent of the formula (I):

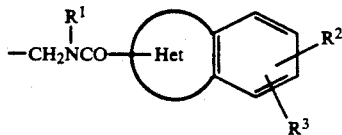
(I)

wherein:
R$^1$ is hydrogen, C$_{1-6}$alkyl optionally substituted by halo, hydroxy, C$_{1-4}$alkoxy, carboxy, amino, cyano, C$_{1-6}$alkanoylamino, phenyl or heteroaryl, or R$^1$ is C$_{2-6}$alkenyl;

Het is a 5- or 6-membered heterocyclic ring selected from a group of the formulae II-III:

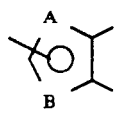
II

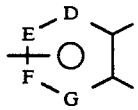
III wherein A is CH or a nitrogen atom; B is oxygen, sulphur or a group NR$^4$; one or two of D, E, F and G are nitrogen atoms and the remainder are CH groups:

or Het is a pyrazinone, pyridinone, pyridazinone or pyrimidinone ring, or is a thione equivalent of such a ring, said rings having a substituent R$^4$ on one nitrogen atom:

or Het is a pyranone or pyranthione ring:

the ring Het being fused by any two adjacent carbon atoms to the bezene ring; and Het being bonded via a carbon atom to the —CH$_2$NR$^1$CO— group;

R$^2$ is hydroxy or an in vivo hydrolysable ester thereof;

R$^3$ is ortho to R$^2$ and is hydroxy or an in vivo hydrolysable ester thereof;

R$^4$ is hydrogen or hydroxy, or C$_{1-6}$alkoxy, phenoxy, C$_{2-6}$alkenyl or C$_{1-6}$alkyl, (any of these groups being optionally substituted by hydroxy, C$_{1-6}$alkoxy, cyano, amino, C$_{1-6}$alkylamino, di-C$_{1-6}$alkylamino, carboxy, C$_{1-6}$alkoxycarbonyl, C$_{1-6}$alkanoyloxy, carbamoyl, C$_{1-6}$alkylcarbamoyl, di-C$_{1-6}$alkylcarbamoyl, C$_{1-6}$-alkoxycarbonylamino, phenyl, phenylC$_{1-6}$alkyl, carboxyaminocarbonyl, C$_{1-6}$alkoxycarbonylaminocarbonyl, benzoyl or C$_{3-8}$cycloalkyl) or R$^4$ is phenyl, C$_{3-8}$ cycloalkyl, amino, C$_{1-6}$alkylamino or di-C$_{1-6}$alkylamino: wherein the fused Het-benzene ring system and/or any phenyl group is further optionally substituted by at least one substituent selected from C$_{1-6}$alkyl, halo, hydroxy, hydroxy C$_{1-6}$alkyl, cyano, trifluoromethyl, nitro, amino, C$_{1-6}$alkylamino, di-C$_{1-6}$alkylamino, phenyl C$_{1-6}$alkylamino, C$_{1-6}$alkanoyl, C$_{1-6}$alkoxy, C$_{1-6}$alkylthio, C$_{1-6}$alkanoyloxy, carbamoyl, C$_{1-6}$alkylcarbamoyl, di-C$_{1-6}$alkyl carbamoyl, carboxy, carboxy C$_{1-6}$alkyl, C$_{1-6}$alkoxycarbonylC$_{1-6}$alkyl, sulpho, sulphoC$_{1-6}$alkyl, sulphonamido, C$_{1-6}$alkylsulphonamido, C$_{1-6}$-alkoxycarbonyl, C$_{1-6}$alkanoylamino, thioureido and amidino.

In one aspect R$^1$ may be C$_{1-6}$alkyl substituted by heteroaryl. Suitably such a heteroaryl group is a 5- or 6-membered ring containing 1, 2 or 3 heteroatoms selected from nitrogen, oxygen and sulphur and may be optionally substituted, for example by the substituents described hereinbefore with respect to the fused Het-benzene ring system. For example R$^1$ may be pyridinylmethyl or furanylmethyl.

Particular meanings for R$^1$ are hydrogen, C$_{1-6}$alkyl for example methyl, ethyl or propyl, hydroxy C$_{1-6}$alkyl for example 2-hydroxyethyl, halo C$_{1-6}$alkyl for example 2-chloroethyl or 2-fluoroethyl, C$_{1-6}$alkoxy C$_{1-6}$alkyl for example 2-methoxyethyl, 2-ethoxyethyl or methoxymethyl, carboxy C$_{1-6}$alkyl for example carboxymethyl, phenyl C$_{1-6}$alkyl for example benzyl or phenethyl, or C$_{2-6}$alkenyl for example allyl.

Preferably R$^1$ is hydrogen, methyl or ethyl. Most preferably R$^1$ is hydrogen.

In one aspect Het is a ring of the formula II as hereinbefore described, that is Het is an imidazole, thiazole, oxazole, pyrrole, furan or thiophen ring. In particular the Het-benzene fused ring system is benzimidazol-2-yl, benzthiazol-2-yl or indol-2-yl.

In another aspect Het is a ring of the formula III as hereinbefore described, that is the Het-benzene fused ring system represents quinoline, isoquinoline, quinazoline, cinnoline, quinoxaline or phthalazine.

In a further aspect Het is a pyrazinone, pyridinone, pyridazinone or pyrimidinone ring, or the thione equivalent of such rings, said rings having a substituent $R^4$ on one nitrogen atom. For example the Het-benzene fused ring system may be of the sub-formula i)-ix):

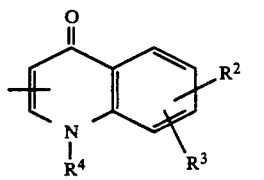  i)

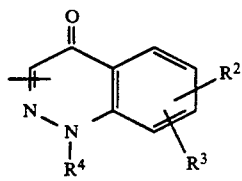  ii)

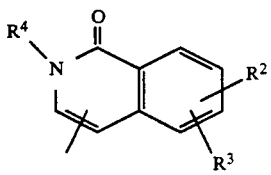  iii)

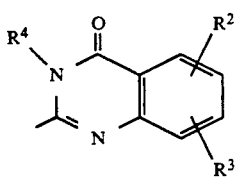  iv)

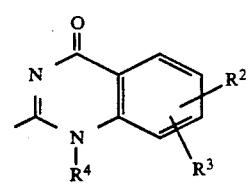  v)

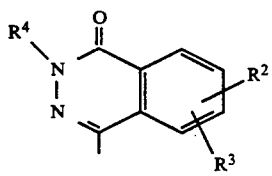  vi)

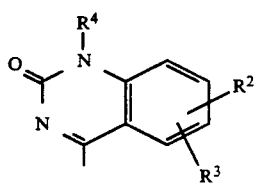  vii)

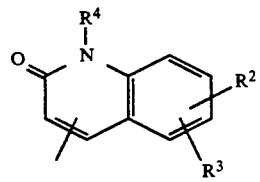  viii)

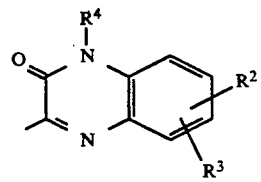  ix)

Particular meanings of the group $R^4$ are hydrogen, hydroxy, $C_{1-6}$alkoxy for example methoxy or ethoxy, $C_{1-6}$alkyl for example methyl, ethyl, n-propyl, isopropyl, n-butyl or isobutyl $C_{3-8}$cycloalkyl for example cyclopropyl, hydroxy $C_{1-6}$alkyl for example hydroxymethyl or hydroxyethyl, phenyl, phenyl$C_{1-6}$alkyl for example benzyl or phenethyl, $C_{2-6}$alkenyl for example allyl, amino$C_{2-6}$alkyl for example aminoethyl or aminopropyl, carbamoyl$C_{1-6}$alkyl for example carbamoylmethyl, $C_{1-6}$alkoxycarbonyl$C_{1-6}$alkyl for example ethoxycarbonylmethyl or ethoxycarbonylethyl and carboxyl$C_{1-6}$alkyl for example carboxymethyl or carboxyethyl. Preferably $R^4$ is hydrogen, methoxy, ethoxy, methyl, ethyl, isopropyl, butyl or benzyl.

Preferred values for the Het-benzene fused ring system are those of the sub-formulae i), ii) and iii).

For the avoidance of doubt, thione equivalents of ring systems i)-ix) are those wherein the oxo group (=O) is replaced by the thioxo group (=S).

In another aspect the Het ring is a pyranone ring so that values of the Het-benzene fused ring system include sub-formulae x)-xii):

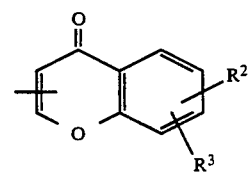  x)

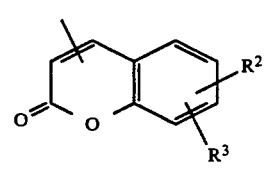  xi)

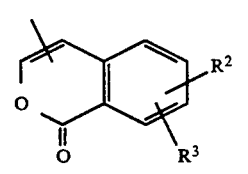  xii)

The ring systems of the sub-formulae xi) are preferred, that is the chroman-2-one ring system. The present invention also covers the related ring systems wherein the oxo group (=O) is replaced by a thione group (=S).

$R^2$ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$ alkanoyloxy for example acetoxy, propionyloxy, pivaloyloxy, $C_{1-4}$alkoxycarbonyloxy for example ethoxycarbonyloxy, phenylacetoxy and phthalidyl.

Conveniently both $R^2$ and $R^3$ have the same value and are both hydroxy or are both in vivo hydrolysable esters, for example they are both acetoxy or pivaloyloxy.

As stated hereinbefore the fused Het-benzene ring system may be further optionally substituted, on either ring, by one or more atoms or groups. Particular substituents are $C_{1-6}$alkyl for example methyl or ethyl, halo for example chloro, fluoro or bromo, hydroxy, hydroxy$C_{1-6}$alkyl for example hydroxyethyl, nitro, amino, $C_{1-6}$alkylamino for example methylamino or ethylamino, di-$C_{1-6}$alkyl amino for example dimethylamino or diethylamino, phenyl$C_{1-6}$alkylamino for example benzylamino, $C_{1-6}$alkoxy for example methoxy or ethoxy, carboxy$C_{1-6}$alkyl for example carboxymethyl, $C_{1-6}$alkanoylamino for example acetamido, trifluoromethyl, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkanoyl for example acetyl, $C_{1-6}$alkylthio for example methylthio, cyano and $C_{1-6}$alkoxycarbonyl for example methylcarbonyl.

In a particularly preferred aspect the 3-position substituent for the cephalosporins of the present invention is of the sub-formula xiii):

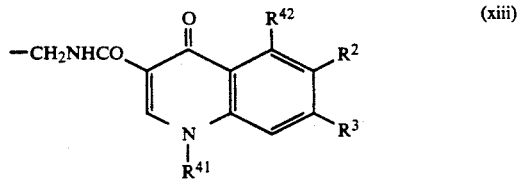

wherein $R^2$ and $R^3$ are as hereinbefore defined, $R^{41}$ is hydrogen or $C_{1-6}$ alkyl for example methyl, ethyl, propyl or butyl and $R^{42}$ is hydrogen, nitro, cyano, chloro, bromo, carboxy or $C_{1-6}$ alkoxycarbonyl for example methoxycarbonyl or ethoxycarbonyl.

In a further particularly preferred aspect the 3-position substituent for the cephalosporins of the present invention is of the sub-formula xiv):

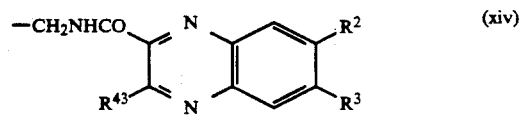

wherein $R^{43}$ is hydrogen, chloro, bromo, carboxy, $C_{1-6}$ alkoxycarbonyl for example methoxycarbonyl or ethoxycarbonyl, amino, $C_{1-6}$ alkylamino for example methylamino or ethylamino or phenyl $C_{1-6}$alkylamino for example benzylamino.

In another particularly preferred aspect the 3-position substituent for the cephalosporins of the present invention is of the sub-formula xv) or xvi):

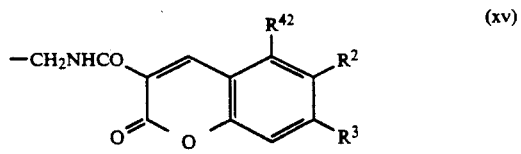

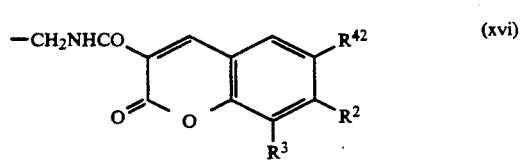

wherein $R^2$, $R^3$ and $R^{42}$ are as hereinbefore defined.

As stated hereinbefore the present invention relates to cephalosporins having a novel 3-position substituent. A particular class of cephalosporins within the present invention is that of the formula IV:

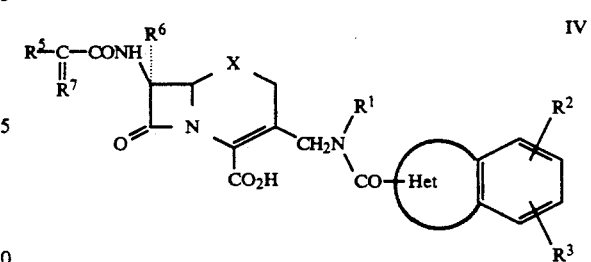

and salts and esters thereof wherein $R^1$, Het, $R^2$ and $R^3$ are as hereinbefore defined;

X is sulphur, oxygen, methylene or sulphinyl;

$R^6$ is hydrogen, methoxy or formamido; and $R^5$ and $R^7$ are groups known for such positions in the cephalosporin art.

Preferably X is sulphur.

Preferably $R^6$ is hydrogen.

$R^5$ is for example 2-aminothiazol-4-yl or 2-aminooxazol-4-yl each optionally substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^7$ is for example of the formula $=N.O.R^8$ (having the syn configuration about the double bond) wherein $R^8$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4C)alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydroxypyran-2-yl, thientan-3-yl, 2-oxopyrrolidinyl, or 2-oxotetrahydrofuranyl, or $R^8$ is of the formula V:

$$-(CH_2)_q-C(COOH)=CR^9R^{10} \qquad V$$

wherein q is one or two and $R^9$ and $R^{10}$ are independently hydrogen or $C_{1-4}$alkyl; or $R^8$ is of the formula VI:

$$—CR^{11}R^{12}—(CH_2)_r—COR^{13} \qquad VI$$

wherein r is 0-3, $R^{11}$ is hydrogen, (1-3C)alkyl or methylthio, $R^{12}$ is hydrogen (1-3C)alkyl, (3-7C)cycloalkyl, cyano, carboxy, (2-5C)carboxyalkyl or methanesulphonylamino, or $R^{11}$ and $R^{12}$ are joined to form, together with the carbon to which they are attached, a (3-7C)carbocyclic ring, and $R^{13}$ is hydroxy, amino, (1-4C)alkoxy, (1-4C) alkylamino or of the formula $NHOR^{14}$ in which $R^{14}$ is hydrogen or (1-4C)alkyl;

or $R^7$ may be of the formula=$CH.R^{15}$ wherein $R^{15}$ is hydrogen, halogen, (1-6C)alkyl, (3-7C)cycloalkyl, (2-6C)alkenyl, (3-7C)cycloalkenyl, phenyl or benzyl.

Particular meanings for $R^8$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, methylcarbamoylmethyl, 2-chloroethyl, 2-fluoroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)ethyl, tetrahydropyran-2-yl, thietan-3-yl, 2-oxopyrrolidinyl and 2-oxotetrahydrofuran-3-yl, or, when $R^8$ is of the formula V in which q is 1 or 2, a particular meaning for $R^8$ is when $R^9$ and $R^{10}$ are hydrogen or methyl, or, when $R^8$ is of the formula VI, a particular meaning for $R^8$ is when $r=0$ and $R^{11}$ is hydrogen, methyl or methylthio, $R^{12}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{11}$ and $R^{12}$ are joined to form, together with the carbon to which they are attached, a cyclopropane, cyclobutane, cyclopentane, cyclohexane or cycloheptane ring and $R^{13}$ is hydroxy, amino, methoxy, ethoxy, methylamino, ethylamino, or of the formula $NHOR^{14}$ in which $R^{14}$ is hydrogen, methyl or ethyl.

Preferably $R^8$ is $C_{1-6}$alkyl for example methyl or ethyl, 1-carboxycyclobutyl, 1-carboxycyclopentyl, or 2-carboxyprop-2-yl. In particular $R^8$ is 2-carboxyprop-2-yl.

Particular meanings for $R^{15}$ are hydrogen, methyl, ethyl or chlorine.

A particularly preferred class of cephalosporins of the present invention is that wherein $R^5$ is 2-aminothiazol-4-yl, $R^7$ is a group $=NOR^8$ wherein $R^8$ is $C_{1-6}$ alkyl, 1-carboxycyclobutyl, 1-carboxcyclopentyl or 2-carboxyprop-2-yl, $R^6$ is hydrogen, X is sulphur and the 3-position substituent is of the sub-formula xiii)–xvi).

Particular compounds of the present invention include:

7-[2-(2-aminothiazol-4-yl)-2-((Z)-1-carboxy-1-methylethoxyimino)acetamido]-3-(1,4-dihydro-6,7-dihydroxy-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-methyl-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-ethyl-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido[-3-(1,4-dihydro-6,7-dihydroxy-1-n-butyl-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-ethyl-5-nitro-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-ethyl-5-cyano-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-ethyl-5-chloro-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-methoxy-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dipivaloyloxy-1-ethyl-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(1,4-dihydro-6,7-dihydroxy-1-ethyl-4-oxocinnolin-3-carboxamidomethyl)ceph-3-em-4-carboxylic acid, 7-[2-(2-aminothiazol-4-yl)-2-((Z)-1-carboxy-1-methylethoxyimino)acetamido]-3-(5-carboxy-1,4-dihydro-6,7-dihydroxy-1-ethyl-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(5-carboxy-1,4-dihydro-6,7-dihydroxy-4-oxoquinolin-3-carboxamidomethyl)ceph-3-em-4-carboxylic acid, 7-[2-(2-aminothiazol-4-yl)-2-((Z)-1-carboxy-1-methylethoxyimino)acetamido]-3-(6,7-dihydroxy-2-methylaminoquinoxalin-3-carboxamidomethyl)ceph-3-em-4-carboxylic acid, 7-[2-(2-aminothiazol-4-yl)-2-((Z)-1-carboxy-1-methylethoxyimino)acetamido]-3-(2-bromo-6,7-dihydroxyquinoxalin-3-carboxamidomethyl)ceph-3-em-4-carboxylic acid, 7-[2-(2-aminothiazol-4-yl)-2-((Z)-1-carboxy-1-methylethoxyimino)acetamido]-3-(2-chloro-6,7-dihydroxyquinoxalin-3-carboxamidomethyl)ceph-3-em-4-carboxylic acid, 7-[2-(2-aminothiazol-4-yl)-2-((Z)-1-carboxy-1-methylethoxyimino)acetamido]-3-(2-benzylamino-6,7-dihydroxyquinoxalin -3-carboxamidomethyl)ceph-3-em-4-carboxylic acid, 7-[2-(2-aminothiazol-4-yl)-2-((Z)-1-carboxy-1-methylethoxyimino)acetamido]-3-(6,7-dihydroxy-2-methoxycarbonyl-quinoxalin-3-carboxamidomethyl)ceph-3-em-4-carboxylic acid 7-[2-(2-aminothiazol-4-yl)-2-((Z)-1-carboxy-1-methylethoxyimino)acetamido]-3-(7,8-dihydroxy-2-oxo-2H-benzopyran-3-carboxamidomethyl)ceph-3-em-4-carboxylic acid, and 7-[2-(2-aminothiazol-4-yl)-2-((Z)-1-carboxy-1-methylethoxyimino)acetamido]-3-(1,4-dihydro-6,7-dihydroxy-2-methyl-1-oxo-isoquinolin-3-carboxamidomethyl)ceph-3-em-4-carboxylic acid.

The cephalosporin derivatives referred to herein are generally named in accordance with the 'cephem' nomenclature and numbering system proposed in J.A.C.S. 1962, 84, 3400.

It should be realised, of course, that the present invention covers all tautomeric forms, for example the sub-formulae i)–ix) are depicted in the keto form; where possible these may exist and be depicted in the enol form. Such tautomers are, of course, within the scope of the present invention. Furthermore the Het ring may be optionally substituted by hydroxy and this may exist in the tautomeric keto form.

As stated hereinbefore the compounds of this invention ar primarily intended for use in therapy. Therefore in a preferred aspect the present invention provides a cephalosporin compound having a 3-position substituent of the formula I or a pharmaceutically acceptable salt or ester thereof. Suitable salts include acid addition salts formed with hydrochloric, hydrobromic, citric, maleic, phosphoric and sulphuric acids. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapy of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal, topical, local or parenteral administration. For these purposes it may be formulated by means known to the art into the form of, for example, tablets, capsules, syrups, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises:

a) reacting a cephalosporin compound having a 3-position substituent of the formula: $-CH_2NHR^1$ wherein $R^1$ is as hereinbefore defined with a compound of the formula VII:

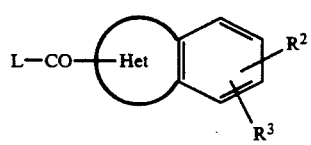

VII wherein Het, $R^2$ and $R^3$ are as hereinbefore defined and L is a leaving group; or b) for compounds of the formula IV, reacting a compound of the formula VIII with a compound of the formula IX or a reactive derivative thereof:

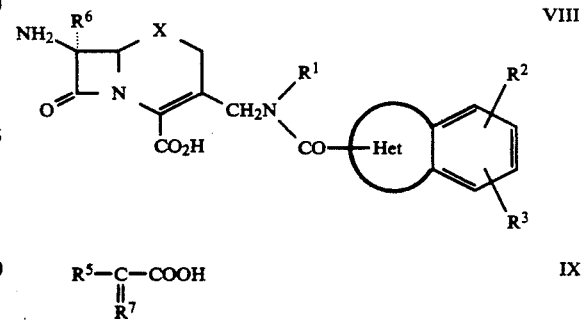

wherein $R^1$, $R^2$, $R^3$, X, Het, $R^5$, $R^6$ and $R^7$ are as hereinbefore defined; or c) for compounds of the formula IV wherein $R^7$ is a group $=NOR^8$, reacting a compound of the formula X:

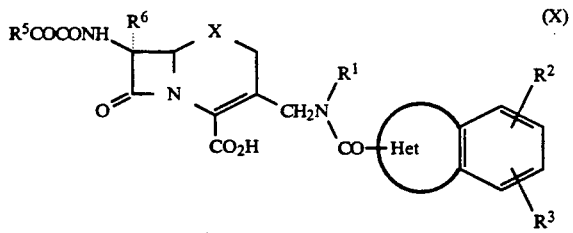

wherein R$^1$, R$^2$, R$^3$, R$^5$, R$^6$, X, and Het are as hereinbefore defined, with a compound of the formula: R$^8$ONH$_2$ wherein R$^8$ is as hereinbefore defined; or d) for compounds of the formula IV wherein R$^7$ is a group =NOR$^8$ and R$^8$ is other than hydrogen, reacting a compound of the formula IV as hereinbefore defined wherein R$^7$ is a group =NOH with a compound of the formula XI:

 XI wherein L$^1$ is a leaving group and R$^{16}$ is a group R$^8$ other than hydrogen; or e) for compounds of the formula IV forming a group R$^5$ by cyclizing an appropriate precursor thereof: wherein any functional groups are optionally protected: and thereafter, if necessary:

i) removing any protecting group,
ii) for preparing in vivo hydrolysable esters, esterifying corresponding hydroxy groups,
iii) converting compounds wherein X is S to compounds wherein X is sulphinyl and vice versa,
iv) forming a pharmaceutically acceptable salt.

In the reaction between a cephalosporin compound having a 3-position substituent of the formula: —CH$_2$NHR$^1$ and a compound of the formula VII, conveniently L is a leaving group such as halo for example chloro, bromo or iodo. Most suitably the reaction is performed under conditions conventional for the reaction of acid halides with amines for example in the presence of an organic amine such as triethylamine. Suitably the reaction is performed at an ambient or lower temperature in a substantially inert solvent such as dimethylformamide and/or dichloromethane. In an alternative aspect the leaving group L is part of an activated ester formed with the acid precursor of the compound of the formula VII, i.e. a compound wherein L is —OH provides an activated ester, e.g. dicyclohexylcarbodi-imide provides an activated ester of the formula VII wherein L is —OC(NHC$_6$H$_{11}$)=NC$_6$H$_{11}$, which group is displaced by the cephalosporin having a 3-position substituent of the formula: —CH$_2$NHR$^1$. Formation and reaction of the active ester is performed in conventional manner in the presence of reaction promotors such as hydroxybenzotriazole and triethylamine, for example in a substantially inert organic solvent such as dimethylformamide at a non-extreme temperature such as 10° C.–50° C.

The cephalosporin starting-materials for this reaction are known from the art, or are made by methods analogous to those of the art. See for example EP-A-127992 and EP-A-164944.

The compounds of the formula VII are either known in the art or are made by methods analogous thereto. For example compounds wherein L is chloro are conveniently prepared from the corresponding acids of the formula (VII A):

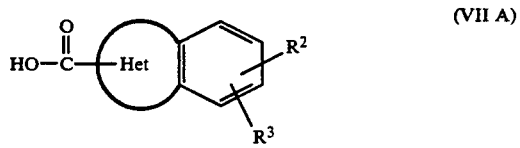

wherein Het, R$^2$ and R$^3$ are as hereinbefore defined. The acids are known or are prepared by methods of heterocyclic chemistry known to those skilled in the art, for example as in the hereinafter described Examples. Many of the acids of the formula VII A are novel and as such form another aspect of the present invention; in particular wherein R$^2$ and R$^3$ are both hydroxy. Suitable and preferred acids of the formula VII A are those that give rise to the suitable and preferred cephalosporin compounds of the present invention. In particular the present invention provides specific, novel heterocyclic carboxylic acids (and precursors thereto) described in the experimental section hereinafter.

The reaction between compounds of the formulae VIII and IX is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula VIII can be prepared in a manner analogous to that described for the compounds having the 3-substituent of the formula I, with the 7-amino group being optionally protected.

The reaction between the compound of the formula X and R$^8$ONH$_2$ is performed under conditions standard in the general chemical and/or cephalosporin art. The compounds of the formula X can be prepared in a manner analogous to that described for the compounds having the 3-substituent of the formula I.

The reaction between the compound of the formula IV wherein R$^7$ is a group =NOH and a compound of the formula XI is performed under conditions standard in the general chemical and/or cephalosporin art.

A group R$^5$ may be formed by cyclizing an appropriate precursor. For example compounds of the formulae XII and XIII:

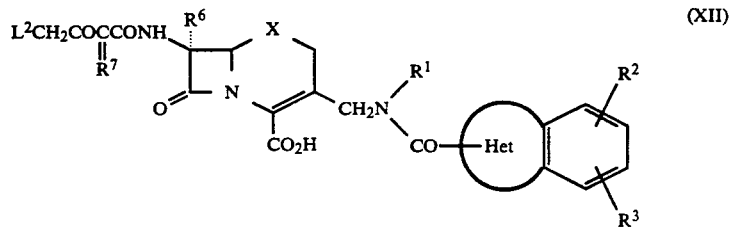

$NH_2CSNH_2$ (XIII)

wherein $R^7$, $R^6$, X, $R^1$, $R^2$, $R^3$ and Het are as hereinbefore defined and $L^2$ is a leaving group, may be reacted to form a 2-aminothiazol-4-yl group. A nitrogen atom of the thiourea may be optionally protected during this cyclization.

The compounds of the formula XII can be prepared in a manner analogous to that described for the compounds having a 3-substituent of the formula I.

The compounds of the formulae IX, XI and $R^8ONH_2$ are known from, or can be made by the methods of, the general chemical and/or cephalosporin art.

The compounds of the formulae VIII, X and XII are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido group.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular, the cephalosporins of the present invention show good stability to $\beta$-lactamases reinforcing the broad spectrum potency. In a further advantageous aspect. The present compounds typically have particularly high activity in vitro against strains of Pseudomonas aeruginosa and other Gram-negative aerobic bacteria.

The antibacterial properties of the compounds of the invention may also be demonstrated in vivo in conventional mouse protection tests.

In addition representative compounds of this invention show prolonged duration, as evidenced by half-life values, in test animals.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in-vitro test system using Isosensitest agar medium. The antibacterial activity is described in terms of the minimum inhibitory concentration (MIC) determined by the agar-dilution technique with an inoculum size of $10^4$ CFU/spot (CFU represents colony forming units).

| ORGANISM | MIC (μg/ml) EXAMPLE | | | | | | | | | | | | | | | |
|---|---|---|---|---|---|---|---|---|---|---|---|---|---|---|---|---|
| | 1 | 2 | 5 | 6 | 7 | 11 | 14 | 17 | 28 | 30 | 33 | 37 | 39 | 42 | 47 | 53 | 59 |
| P.aeruginosa PU21 (A8101028) | 0.03 | 0.06 | 0.008 | 0.015 | 0.03 | 0.03 | 0.015 | 0.008 | 0.015 | 0.008 | 0.015 | 0.03 | 0.008 | 0.015 | 0.03 | 0.015 | 0.008 |
| Ent. cloacae P99 (A8401054) | 0.03 | 0.03 | 0.03 | 0.03 | 0.015 | 0.06 | 0.015 | 0.008 | 0.03 | 0.03 | 0.06 | 0.06 | 0.03 | 0.125 | 0.25 | 0.03 | 0.03 |
| Ser. marcescens (A8421003) | 0.008 | 0.008 | 0.008 | 0.008 | 0.008 | 0.015 | 0.008 | 0.008 | 0.008 | 0.008 | 0.015 | 0.008 | 0.008 | 0.015 | 0.06 | 0.008 | 0.008 |
| M. morganii (A8433001) | 0.015 | 0.06 | 0.03 | 0.015 | 0.015 | 0.06 | 0.008 | 0.008 | 0.015 | 0.03 | 0.25 | 0.015 | 0.03 | 0.015 | 0.5 | 0.015 | 0.008 |
| K. aerogenes (A8391027) | 0.008 | 0.008 | 0.008 | 0.008 | 0.008 | 0.008 | 0.008 | 0.008 | 0.008 | 0.008 | 0.008 | 0.008 | 0.008 | 0.008 | 0.03 | 0.008 | 0.008 |
| E. coli DCO (A8341098) | 0.008 | 0.008 | 0.008 | 0.008 | 0.008 | 0.008 | 0.008 | 0.008 | 0.008 | 0.008 | 0.008 | 0.008 | 0.008 | 0.008 | 0.008 | 0.008 | 0.008 |
| S. aureus 147N (A8601052) | 16 | 1 | 16 | 16 | 2 | 16 | 32 | 4 | 16 | 32 | 64 | 16 | 16 | 8 | 16 | 1 | 16 |
| S. dublin (A8369001) | 0.008 | 0.008 | 0.008 | 0.008 | 0.008 | 0.008 | 0.008 | 0.008 | 0.008 | 0.008 | 0.008 | 0.008 | 0.008 | 0.015 | 0.125 | 0.008 | 0.008 |
| Strep. pyogenes (A681018) | 0.125 | — | 0.25 | 0.25 | 0.03 | 0.25 | 1 | 0.06 | 0.25 | 0.5 | — | 0.25 | 0.06 | 0.125 | 0.125 | 0.03 | 0.5 |

EXAMPLE 1

7-[2-(2-Aminothiazol-4-yl)-2-((Z)-1-carboxy-1-methylethoxyimino)acetamido]-3-(1,4-dihydro-1-ethyl-6,7-dihydroxy-4-oxoquinolin-3-carboxamidomethyl)ceph-3-em-4-carboxylic acid.

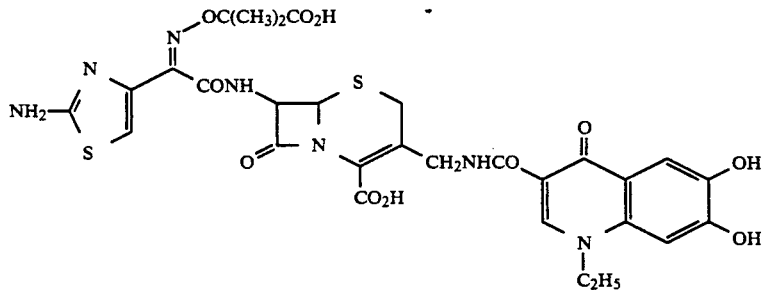

i) 1.4-Dihydro-1-ethyl-6,7-methylenedioxy-4-oxoquinoline-3-carboxylic acid (3.9 g) and boron tribromide (15 ml) were heated at 50° C. for 15 hours. The reaction mixture was cooled and added slowly to water (100 ml) at 0° C. The pH was adjusted to 11 with concentrated potassium hydroxide, the mixture was filtered and the filtrate taken to pH1, whereupon the precipitate was collected by filtration, washed with water and dried to give 1,4-dihydro-6,7-dihydroxy-1-ethyl-4-oxoquinoline-3-carboxylic acid (3.13 g); δ ((CD$_3$)$_2$SO) 1.42(3H,t); 4.46(2H,q); 7.23(1H,s); 7.66(1H,s); 8.82(1H,s)ppm.

ii) Part of the product from i) (1.0 g) was dissolved in acetonitrile (15 ml) by the addition of 1,8-diazabicyclo-[5.4.0]undec-7-ene (1.2 g). The solution was cooled to 0° C., phenacyl chloride (1.3 ml) added and stirred at ambient temperature for 72 hours. HCl solution in ether (40 ml; 40 g/l) was added; the solvents were evaporated and the resultant residue was dissolved in dichloromethane, filtered, concentrated and dissolved in methanol to give 6,7-diphenylacetoxy-1,4-dihydro-1-ethyl-4-oxoquinoline-3-carboxylic acid (0.414 g) as a precipitate; δ(CDCl$_3$) 1.54(3H,t); 3.56 and 3.68(4H,2s); 4.27(2H,q); 7.35(10H,s); 7.52 and 8.28(2H,ss); 8.73(1H,s)ppm.

iii) Part of the product from ii) (0.286 g) was dissolved in anhydrous dichloromethane (10 ml) and treated with thionyl chloride (1.1 equivalents) for 90 minutes to give 6,7-diphenylacetoxy-1,4-dihydro-1-ethyl-4-oxoquinoline-3-carboxylic acid chloride.

iv) The product from iii) was used without purification. To 3-aminomethyl-7-[2-(2-aminothiazol-4-yl)-2-((Z)-1-carboxy-1-methylethoxyimino)acetamido]ceph-3-em-4-carboxylic acid (0.446 g) in dimethylformamide (10 ml), at −20° C., was added triethylamine (3 equivalents) followed by the product of iii) above in dichloromethane (10 ml). The reaction temperature was allowed to reach 0° C. over a period of 60 minutes whereupon the solvents were evaporated to give, as a residue, the 6,7-diphenylacetoxy precursor of the title compound. This residue was dissolved in aqueous methanol, the pH was adjusted to 8.5 using ammonium hydroxide and maintained at this value for 60 minutes. 2N HCl was added to take the mixture to pH6.5 whereupon the crude product was purified by HPLC chromatography on silica using gradient elution (methanol:water:acetic acid 30:69:1 45:54:1). Collection of the appropriate fractions and evaporation gave the title compound (0.110 g); δ ((CD$_3$)$_2$SO/CD$_3$COOD/CF$_3$COOD) 1.4(3H,t); 1.54(6H,s); 3.6(2H,s); 4.24(2H,q); 4.4(2H,m); 5.2(1H,d); 5.82(1H,d); 7.06(1H,s); 7.12, 7.65 and 8.69(3H,3s)ppm.

EXAMPLES 2-63

The following general procedure was used for the preparation of the compounds of Examples 2-63.

To a solution of the appropriate 3-aminomethylcephalosporin in dimethylformamide, at a temperature in the range +10° to −20° C. (generally −20° C.), was added triethylamine (about 2 or 3 equivalents) followed by at least one equivalent of the appropriate heterocycle in the form of an acid chloride in dichloromethane (or an activated este in dimethylformamide where indicated).

The reaction was allowed to proceed to completion (typically 1 to 5 hours), for example as judged by thin layer chromatography or HPLC. The solvent was evaporated under reduced pressure to give the corresponding 3-heterocyclic carboxamidomethyl cephalosporin which was purified by:

i) column chromatography on HP20SS resin using gradient elution with methanol/water/acetic acid (1%) and/or ii) preparative HPLC on $C_{18}$ reverse phase silica using acetonitrile/water/trifluoroacetic acid (0.1%) or methanol/ammonium carbonate buffer.

In certain cases, indicated by footnotes, the hydroxy groups on the heterocycle are protected. In such cases the coupling reaction provides a cephalosporin wherein the hydroxy groups are protected. This may be subjected to standard deprotection (as indicated in footnotes).

Particulars of the compounds prepared are given in Table 1. NMR characterising data are given in Table 2.

TABLE 1

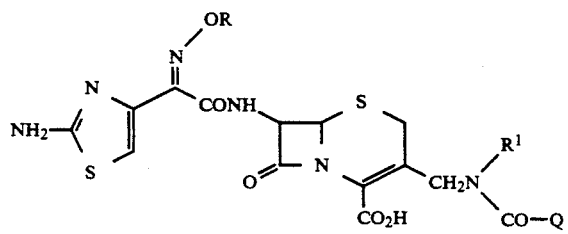

| Example | R | R¹ | Q | Footnotes |
|---|---|---|---|---|
| 2 | Et | H | ![quinolone with Et, OH, OH] | 1 |
| 3 | CMe₂COOH | Et | " | 1 |
| 4 | ![cyclopentyl-COOH] | H | " | 2 |
| 5 | CMe₂COOH | H | ![quinolone with Me, OH, OH] | 2 |
| 6 | CMe₂COOH | H | ![quinolone with Bu$^n$, OH, OH] | 2 |
| 7 | CMe₂COOH | H | ![quinolone with CH₂CH=CH₂, OH, OH] | 2 |

TABLE 1-continued
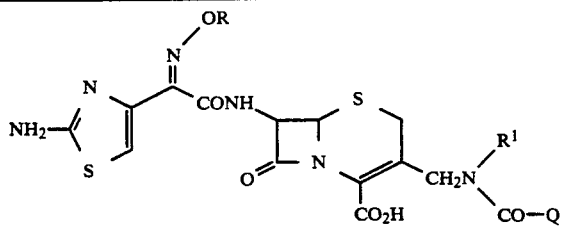
| Example | R | R¹ | Q | Footnotes |
|---|---|---|---|---|
| 8 | CMe₂COOH | H |  | 3 |
| 9 | CH₂CONHMe | H | 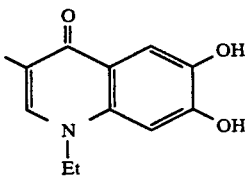 | 4 |
| 10 | CMe₂COOH | H | 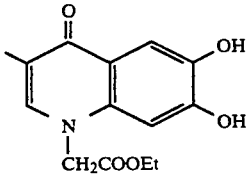 | |
| 11 | CMe₂COOH | H | 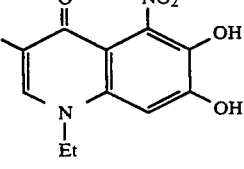 | |
| 12 | Et | H | " | |
| 13 | CMe₂COOH | H | 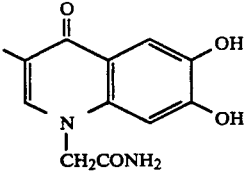 | 4, 5 |
| 14 | CMe₂COOH | H | 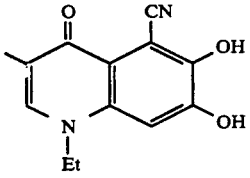 | 6 |
| 15 | CMe₂COOH | H | 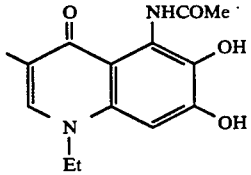 | 6 |

TABLE 1-continued

| Example | R | R¹ | Q | Footnotes |
|---|---|---|---|---|
| 16 | CMe₂COOH | H | 3-methyl-5,8-dimethyl-6,7-dihydroxy-4-oxo-1H-quinoline | |
| 17 | CMe₂COOH | H | 3-methyl-6,7-dihydroxy-4-oxo-1H-quinoline | 1 |
| 18 | CMe₂COOH | H | 3-methyl-6,7-dihydroxy-4-oxo-1-methoxy-quinoline | 1 |
| 19 | Et | H | 3-methyl-6,7-dihydroxy-4-oxo-1-(carboxymethyl)quinoline | 7 |
| 20 | CMe₂COOH | H | 3-methyl-7,8-dihydroxy-4-oxo-1-ethylquinoline | 5 |
| 21 | CMe₂COOH | H | 2-methyl-6,7-dihydroxy-4-oxo-quinoline | 8 |
| 22 | CMe₂COOH | H | 3-methyl-6-acetoxy-7-hydroxy-4-thioxo-1-ethylquinoline | |
| 23 | CMe₂COOH | H | 3-methyl-6,7-dihydroxy-1-oxoisoquinoline | 8, 9 |

TABLE 1-continued
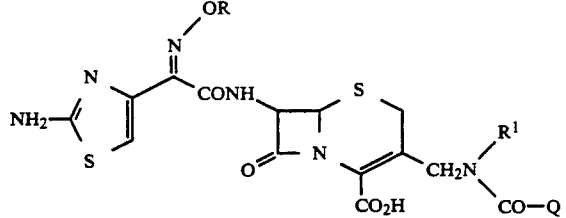
| Example | R | R¹ | Q | Footnotes |
|---|---|---|---|---|
| 24 | CMe₂COOH | H | 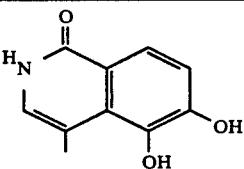 | 8 |
| 25 | CMe₂COOH | H | 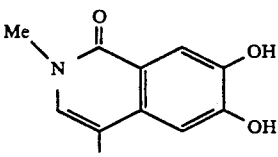 | 8 |
| 26 | Et | H | 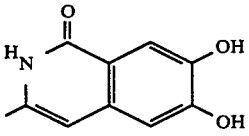 | 8 |
| 27 | CMe₂COOH | H | 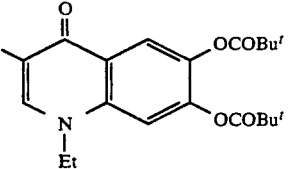 | |
| 28 | CMe₂COOH | H | 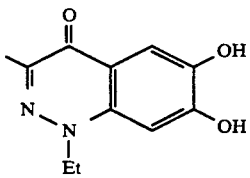 | 1 |
| 29 | Et | H | " | 1 |
| 30 | CMe₂COOH | H | 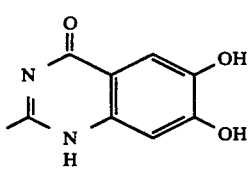 | 8 |
| 31 | CMe₂COOH | H | 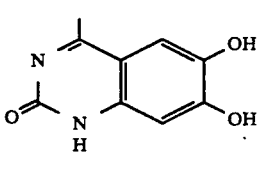 | 8 |
| 32 | Et | H | 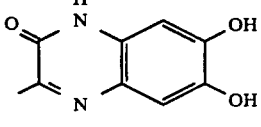 | 8 |

TABLE 1-continued

| Example | R | R¹ | Q | Footnotes |
|---|---|---|---|---|
| 33 | CMe₂COOH | H | " | 8 |
| 34 | CMe₂COOH | H | (2-methyl-acrylamido-4,5-dihydroxyphenyl) | 1 |
| 35 | CMe₂COOH | H | (4-methyl-6,7-dihydroxyquinazolinyl) | 8 |
| 36 | CMe₂COOH | H | (2-methyl-6,7-dihydroxyquinolinyl) | 8 |
| 37 | CMe₂COOH | H | (4-chloro-2-methyl-6,7-dihydroxyquinolinyl) | 8 |
| 38 | CMe₂COOH | H | (4-NMe₂-2-methyl-6,7-dihydroxyquinolinyl) | 8 |
| 39 | CMe₂COOH | H | (3-methyl-6,7-dihydroxyquinoxalinyl) | 8 |
| 40 | CMe₂COOH | H | (2-amino-3-methyl-6,7-dihydroxyquinoxalinyl) | 8 |
| 41 | CMe₂COOH | H | (2-benzylamino-3-methyl-6,7-dihydroxyquinoxalinyl) | 8 |
| 42 | CMe₂COOH | H | (2-methylamino-3-methyl-6,7-dihydroxyquinoxalinyl) | 8 |

TABLE 1-continued
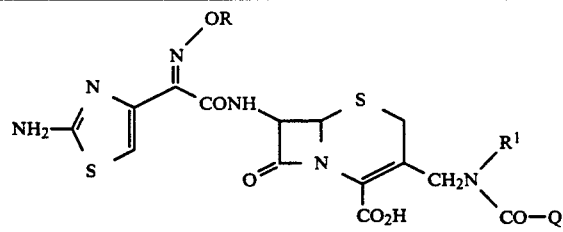
| Example | R | R¹ | Q | Footnotes |
|---|---|---|---|---|
| 43 | CMe₂COOH | H | (X = Br, Cl) | 8 |
| 44 | CMe₂COOH | H | | 8 |
| 45 | CMe₂COOH | H | | 10 |
| 46 | CMe₂COOH | H | | 8 |
| 47 | CMe₂COOH | H | | 11 |
| 48 | CMe₂COOH | H | | 12 |
| 49 | CMe₂COOH | H | | 8 |
| 50 | CMe₂COOH | H | | 8 |
| 51 | CMe₂COOH | H | | 13, 14 |

TABLE 1-continued
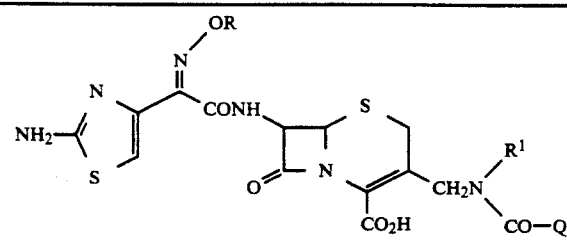
| Example | R | R¹ | Q | Footnotes |
|---------|---|----|---|-----------|
| 52 | CMe₂COOH | H | 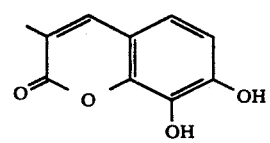 | 13, 14 |
| 53 | Et | H | " | 13 |
| 54 | CMe₂COOH | H | 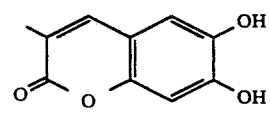 | 13, 15 |
| 55 | CMe₂COOH | H | 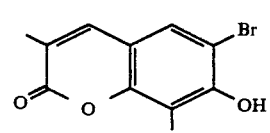 | 13 |
| 56 | Et | H | 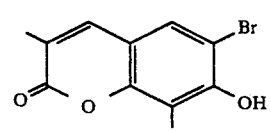 | 13 |
| 57 | CMe₂COOH | H | 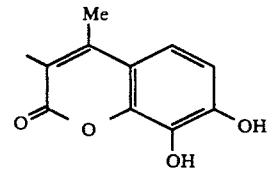 | 13, 15 |
| 58 | CMe₂COOH | H | 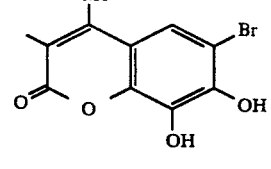 | 13, 15 |
| 59 | CMe₂COOH | H | 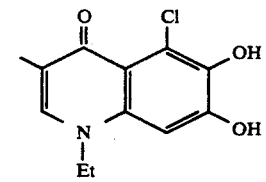 | 16 |
| 60 | Et | H | " | 16 |
| 61 | CMe₂COOH | H | 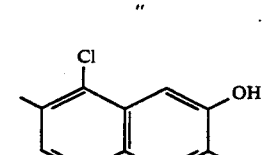 | 11, 17 |

TABLE 1-continued

[Structure: core cephalosporin with aminothiazole oxime side chain, showing OR, CONH, CO₂H, CH₂N(R¹)CO—Q substituents]

| Example | R | R¹ | Q | Footnotes |
|---|---|---|---|---|
| 62 | CMe₂COOH | H | [quinolinone with OCOMe, OH, methyl, NH substituents] | 11, 17 |
| 63 | CMe₂COOH | H | [isoquinolinone with Me-N, two OH groups] | 8 |

Footnotes to Table 1

1 The coupling reaction was performed with a carbonyl chloride wherein the hydroxy groups were protected as acetoxy to provide the corresponding cephalosporin. This was deprotected by dissolving in aqueous methanol, adjusting the pH to 8.5 with ammonium hydroxide, maintaining this value for 60 minutes and subsequently adjusting the pH to 6.5 to give the corresponding dihydroxy cephalosporin.
2 6N HCl is added to the reaction mixture prior to evaporation of the solvent.
3 The reaction was performed on the t-butoxycarbonyl derivative of 1-aminoethyl-6,7-dihydroxy-4-oxoquinolin-3-yl carbonyl chloride. The corresponding cephalosporin was purified by HP2OSS chromatography and subsequently deprotected with trifluoroacetic acid (stirring for 30 minutes followed by evaporation).
4 Trifluoroacetic acid was added to the reaction mixture prior to the evaporation of the solvent.
5 The reaction was performed with silylated 3-aminomethyl cephalosporin.
6 Purification by standard chromatography followed by HPLC chromatography using ammonium carbonate buffer and methanol as eluent.
7 The reaction was performed on the t-butoxycarbonyl derivative of 1-carboxymethyl-6,7-dihydroxy-4-oxoquinolin-3-yl carbonyl chloride. The corresponding cephalosporin was purified by HP2OSS chromatography and subsequently deprotected with trifluoroacetic acid (stirring for up to 2 hours followed by evaporation).
8 The heterocyclic compound was reacted in the form of an activated ester (corresponding carboxylic acid reacted with dicyclohexylcarbodi-imide and hydroxybenzotriazole in dimethylformamide). The coupling reaction with the 3-aminomethylcephalosporin and triethylamine was performed at about 15–50° C. for up to about 2–3 hours.
9 Purification on HP2OSS resin using ammonium buffer and methanol as eluent.
10 Reaction performed in aqueous acetonitrile containing triethylamine. The pH was then adjusted to 7 and, after about 1 hour, the solution was acidified to pH4 and purified.
11 Active ester formed with N-hydroxysuccinimide and reacted with 3-aminomethyl cephalosporin in dimethylsulphoxide in the presence of triethylamine.
12 Reaction performed on 6,7-diacetoxyisocoumarin in tetrahydrofuran/methanol. Deprotection at pH 8.5 with aqueous ammonia.
13 The acid chloride protected as the diacetoxy derivative was reacted with the 3-aminomethyl cephalosporin in dimethylformamide/dichloromethane in the presence of N-methylmorpholine (3 equivalents). The mixture was stirred at 20° C. for 2 hours, concentrated, diluted with water and taken to pH 3.5 whereupon the resultant solid was collected by filtration. This was suspended in water and the acetoxy groups cleaved at pH 8.5.
14 In Examples 51 and 52 the reaction was performed in 1:1 acetonitrile/water in the presence of 2 equivalents of N-methylmorpholine. pH was maintained at 6.0–6.7 throughout the reaction by addition of N-methylmorpholine.
15 The cephalosporin was 3-aminomethyl 7-[2-(aminothiazol-4-yl)-2-((Z)-1-t-butoxycarbonyl-1-methylethoxyimino)acetamide]ceph-3-em-4-carboxylic acid. The t-butoxy carbonyl group was subsequently cleaved by stirring the protected product in 90% aqueous trifluoroacetic acid at 0° C. for 1 hour. Cleavage of the acetoxy groups was performed thereafter.
16 2N HCl is added to the reaction mixture prior to evaporation of the solvent.
17 On completion of the reaction, dicyclohexyl urea filtered off, acetic acid added, solvent reduced in volume and added to water containing sodium acetate. The resultant solution was purified on HP2OSS with acetonitrile - water mixtures.

TABLE 2

NMR data for the compounds of Table 1
taken at 90, 200 or 250 MHz in:
Solvent A:- $(CD_3)_2SO/CD_3COOD/CF_3COOD$
Solvent B:- $(CD_3)_2SO/CD_3COOD$
Solvent C:- $(CD_3)_2SO$
Solvent D:- $(CD_3)_2SO/CF_3COOD$

| Example | Delta Values (ppm) |
|---|---|
| 2 | 1.25 and 1.37(2t, 6H); 3.6(s, 2H); 4.0–4.75(m, 6H); 5.15(d, 1H); 5.75(d, 1H); 7.0(s, 1H); 7.1(s, 1H); 7.63(s, 1H); 8.67(s, 1H). (Solvent A) |
| 3 | 1.04(t, 3H); 1.4(t, 3H); 1.56(s, 6H); 3.4(q, 2H); 3.58(m, 2H); 4.2–4.7(m, 4H); 5.16(d, 1H); 5.82(d, 1H); 7.06(s, 1H); 7.3(s, 1H); 7.7(s, 1H); 8.52(s, 1H). (Solvent A) |
| 4 | 1.4(t, 3H); 1.6–2.4(m, 8H); 3.5–3.75(2d, 2H); 3.95–4.4(m, 4H); 5.2(d, 1H); 5.85(d, 1H); 7.05(s, 1H); 7.12, 7.65 and 8.68(3s, 3H). (Solvent A) |
| 5 | 1.55(s, 6H); 3.60(s, 2H); 3.87(s, 3H); 4.05 and 4.3(2d, 2H); 5.15(d, 1H); 5.85(d, 1H); 7.05(s, 1H): 7.0, 7.2 and 8.6(3s, 3H). (Solvent A) |
| 6 | 0.95(t, 3H); 1.15–2.0(m, 2H); 3.6(s, 2H); 3.95–4.6(m, 4H); 5.15(d, 1H); 5.85(d, 1H); 7.1(s, 2H); 7.63(s, 1H); 8.65(s, 1H). (Solvent A) |

Solvent A:- $(CD_3)_2SO/CD_3COOD/CF_3COOD$
Solvent B:- $(CD_3)_2SO/CD_3COOD$
Solvent C:- $(CD_3)_2SO$
Solvent D:- $(CD_3)_2SO/CF_3COOD$

| Example | Delta Values (ppm) |
|---|---|
| 7 | 1.53(s, 6H); 3.6(s, 2H); 4.08 and 4.48(2d, 2H); 5.14(d, 1H); 5.82(d, 1H); 4.96(s, 2H); 5.24(d, 2H); 6.0(m, 1H); 7.05(s, 2H); 7.64(s, 1H); 8.66(s, 1H). (Solvent A) |
| 8 | 1.55(s, 6H); 3.3(s, 2H); 3.5–3.75(m, 2H); 4.15(s, 2H); 4.35–4.70(m, 2H); 5.15(d, 1H); 5.85(d, 1H); 7.05(s, 1H); 7.17, 7.68 and 8.66(3s, 3H). (Solvent C) |
| 9 | 1.4(t, 3H); 2.65(s, 3H); 3.5–3.75(2d, 2H); 4.0–4.55(2m, 4H); 4.65(s, 2H) 5.2(d, 1H); 5.85(d, 1H); 7.12(s, 1H); 7.12, 7.65, 8.7(3s, 3H). (Solvent A) |
| 10 | 1.19(t, 3H); 1.52(s, 6H); 3.60(s, 2H); 4.17(q, 2H); 4.05 and 4.5(2d, 2H): 5.16(d, 1H); 5.84(d, 1H); 5.19(s, 2H); 7.05(s, 1H); 6.82, 7.64 and 8.69(3s, 3H). (Solvent A) |
| 11 | 1.2–1.5(m, 3H); 1.5(s, 6H); 3.5–3.75(m, 2H); 3.9–4.6(m, 4H); 5.1(d, 1H); 5.8(d, 1H); 7.0(s, 1H); 7.25(s, 1H); 8.7(s, 1H). (Solvent A) |
| 12 | 1.16(m, 6H); 3.5(d, 1H); 3.75(d, 1H); 3.9–4.65(m, 6H); 5.15(d, 1H); 5.8(d, 1H); 6.99(s, 1H); 7.27(s, 1H); 8.74(s, 1H). (Solvent A) |
| 13 | 1.53(s, 6H); 3.6(s, 2H); 4.1 and 4.5(2d, 2H); 5.0(s, 1H); 5.2(d, 1H); 5.85(d, 1H); 7.05(s, 1H); 6.87, 7.63 and 8.63(3s, 3H). (Solvent A) |
| 14 | 1.25–1.6(m, 9H); 3.4–3.8(m, 3H); 3.85–4.7(m, 4H); 5.2(d, 1H); 5.85(d, 1H); 7.05(s, 1H); 7.35(s, 1H); 8.7(s, 1H). (Solvent A) |
| 15 | 1.25–1.6(m, 9H); 2.25(s, 3H); 3.4–3.85(m, 2H); 4–4.7 (m, 4H); 5.15(d, 1H); 5.8(d, 1H); 7.0(s, 1H); 8.7(s, 1H). (Solvent A) |
| 16 | 1.1–1.4(m, 3H); 1.5(s, 6H); 2.4(s, 3H); 2.7(s, 3H); 3.5–3.8(m, 2H); 4–4.7(m, 4H); 5.2(d, 1H); 5.85(d, 1H); 7.05(s, 1H); 8.6(s, 1H). (Solvent A) |
| 17 | 1.53(s, 6H); 3.6(s, 2H); 4.12 and 4.52(2d, 2H); 5.14(d, 1H); 5.82(d, 1H); 7.05(s, 1H); 7.08(s, 1H); 7.53(s, 1H); 8.68(s, 1H); (Solvent A) |
| 18 | 1.44(s, 3H); 1.47(s, 3H); 3.5(d, 1H, J=17.5Hz); 3.67(d, 1H, J=17.5Hz); 4.03(d, 1H, J=14.5Hz); 4.12(s, 3H); 4.43(d, 1H, J=14.5Hz); 5.13(d, 1H, J=5Hz); 5.85(d, 1H J=5Hz); 6.78(s, 1H); 7.08(s, 1H); 7.58(s, 1H); 8.82(s, 1H). (Solvent B) |
| 19 | 1.25(t, 3H); 3.6(m, 2H); 3.8–4.6(m, 4H); 5–5.25(m, 3H); 5.75(d, 1H); 6.8(s, 1H); 7.0(s, 1H); 8.7(s, 1H). (Solvent B) |
| 20 | 1.4(t, 3H); 1.49(s, 3H); 1.51(s, 3H); 3.58(d, 1H); 3.74(d, 1H); 4.08(d, 1H); 4.5(d, 1H); 4.74(q, 2H); 5.19(d, 1H); 5.82(d, 1H); 6.9(s, 1H); 7.11(d, 1H); 7.8(d, 1H); 8.62(s, 1H). (Solvent D) |
| 21 | 1.55(s, 6H); 3.3–3.8(m, 2H); 4.1–4.8(m, 2H); 5.1(d, 1H); 5.8(d, 1H); 7.0(s, 1H); 7.4(s, 1H); 7.5(s, 1H); 7.7(s, 1H). (Solvent A) |
| 22 | 1.44(t, 3H); 1.49(s, 3H); 1.52(s, 3H); 2.32(s, 3H); 3.56(d, 1H); 3.73(d, 1H); 4.14(dd, 1H); 4.52(m, 3H); 5.18(d, 1H); 5.85(dd, 1H); 7.03(s, 1H); 7.34(s, 1H); 8.17(s, 1H); 9.00(s, 1H); 9.70(d, 1H). (Solvent D) |
| 23 | 1.55(m, 6H); 3.45(d, 1H); 3.73(d, 1H); 4.2(d, 1H); 4.56(d, 1H); 5.18(d, 1H); 5.84(d, 1H); 7.03(s, 1H); 7.06(s, 1H); 7.20(s, 1H); 7.57(s, 1H). (Solvent A) |
| 24 | 1.53(m, 6H); 3.4–3.8(m, 2H); 4.13(d, 1H); 4.52(d, 1H); 5.15(d, 1H); 5.8(d, 1H); 6.56(d, 1H); 7.06(s, 1H); 7.21(d, 1H); 8.78(s, 1H). (Solvent A) |
| 25 | 1.54(m, 6H); 3.48(s, 3H); 3.5–3.7(m, 2H); 4.15(d, 1H); 4.52(d, 1H); 5.16(d, 1H); 5.84(d, 1H); 7.08(s, 1H); 7.55–7.70(m, 3H). (Solvent A) |
| 26 | 1.27(t, 3H); 3.25–3.85(m, 2H); 3.95–4.7(m, 4H); 5.15(d, 1H); 5.76(d, 1H); 7.03(m, 2H); 7.23(s, 1H); 7.58(s, 1H). (Solvent A) |
| 27 | 1.25–1.65(m, 27H); 3.4–3.9(m, 2H); 3.95–4.6(m, 4H); 5.16(d, 1H); 5.85(d, 1H); 7.05(s, 1H); 7.73(s, 1H); 8.08(s, 1H); 8.84(s, 1H). (Solvent A) |
| 28 | 1.5(m, 9H); 3.65(s, 2H); 4–4.8(m, 4H); 5.14(d, 1H); 5.8(d, 1H); 7.07(s, 1H); 7.22(s, 1H); 7.56(s, 1H). (Solvent A) |
| 29 | 1.0–1.7(m, 6H); 3.65(s, 2H); 4.0–4.8(m, 6H); 5.17(d, 1H); 5.75(d, 1H); 6.99(s, 1H); 7.21(s, 1H); 7.55(s, 1H). (Solvent A) |
| 30 | 1.55(2s, 6H); 3.4–3.7(m, 2H); 4–4.7(m, 2H); 5.15(d, 1H); 5.85(d, 1H); 7.06(s, 1H); 7.11(s, 1H); 7.46(s, 1H). (Solvent A) |
| 31 | 1.55(s, 6H); 3.5–3.8(m, 2H); 4–4.7(m, 2H); 5.2(d, 1H); 5.9(d, 1H); 6.85(s, 1H); 7.35(s, 1H); 7.05(s, 1H). (Solvent D) |
| 32 | 1.1–1.5(m, 3H); 3.4–3.8(m, 2H); 4–4.7(m, 4H); 5.15(d, 1H); 5.75(d, 1H); 6.85(s, 1H); 6.9–7.4(m, 2H) (Solvent A) |
| 33 | 1.54(s, 6H); 3.6(br, 2H); 4.2 and 4.5(AB, 2H); 5.15(d, 1H); 5.8(d, 1H); 6.8(s, 1H); 7–7.5(m, 2H). (Solvent A) |
| 34 | 1.44(s, 3H); 1.47(s, 3H); 3.58(dd, 2H); 4.0(d, 1H); 4.45(d, 1H); 5.14(d, 1H); 5.85(d, 1H); 6.74(s, 1H); 6.83(s, 1H); 7.12(s, 1H); 7.75(s, 1H); 8.58(s, 1H). (Solvent B) |
| 35 | 1.55(2s, 6H); 3.4–3.8(m, 2H); 4–4.8(m, 2H); 5.2(d, 1H); 5.85(d, 1H); 7.05(s, 1H); 7.36(s, 1H); 8.39(s, 1H); 9.2(s, 1H). (Solvent D) |
| 36 | 1.5(s, 6H); 3.3–3.8(m, 2H); 4.1–4.8(m, 2H); 5.1(d, 1H); 5.8(d, 1H); 7.05(s, 1H); 7.4(s, 1H); 7.8(s, 1H); 8.1(d, 1H); 8.7(d, 1H). (Solvent A) |
| 37 | 1.52(s, 6H); 3.6(m, 2H); 4.2(d, 1H); 4.65(d, 1H); 5.15(d, 1H); 6.8(d, 1H); 7.05(s, 1H); 7.05(s, 1H); 7.5(s, 1H); 7.59(s, 1H); 8.14(s, 1H). (Solvent A) |
| 38 | 1.55(s, 6H); 3.37(s, 6H); 3.6(m, 2H); 4.3(d, 1H); 4.7(d, 1H); 5.1(d, 1H); 5.8(d, 1H); 7.06(s, 1H); 7.27(s, 1H); 7.61(s, 1H). (Solvent A) |
| 39 | 1.54(s, 6H); 3.6(br, 2H); 4.2 and 4.6(AB, 2H); 5.15(d, 1H); 5.8(d, 1H); 7.06(s, 1H); 7.4(s, 2H); 9.15(a, 1H). (Solvent A) |
| 40 | 1.54(s, 6H); 3.4–3.8(m, 2H); 4.2(d, 1H); 4.6(d, 1H); 5.15(d, 1H); 5.85(d, 1H); 7.05(s, 1H); 7.15(s, 1H); 7.30(s, 1H). (Solvent A) |
| 41 | 1.54(s, 6H); 3.4–3.7(m, 2H); 4.15(d, 1H); 4.6(d, 1H); 4.8(s, 2H); 5.15(d, 1H); 5.85(d, 1H); 7.05(s, 1H); 7.2(s, 1H); 7.27(s, 1H); 7.3–7.5(br, 5H) (Solvent A) |
| 42 | 1.54(s, 6H); 3.1(s, 3H); 3.4–3.7(br, 2H); 3.9–4.8(m, 2H); 5.1(d, 1H); 5.8(d, 1H); 7.05(s, 1H); 7.3(s, 1H); 7.35(s, 1H). (Solvent A) |
| 43 | 1.54(m, 6H); 3.4–3.9(m, 2H); 4.18(d, 1H); 4.55(d, 1H); 5.19(d, 1H); 5.83(d, 1H); 7.07(s, 1H); 7.23(s, 1H); 7.27(s, 1H); 7.29(s, 1H). (Solvent A) |
| 44 | 1.55(s, 6H); 3.3–3.9(m, 2H); 4.15(d, 1H); 4.55(d, 1H); 5.15(d, 1H); 5.8(d, 1H); 7.05(s, 1H); 7.34(s, 2H). (Solvent A) |
| 45 | 1.54(s, 6H); 2.34(s, 6H); 3.35–3.85(m, 2H); 4.2(d, 1H); 4.6(d, 1H); 5.15(d, 1H); 5.8(d, 1H); 7.07(s, 1H); 8.1(s, 2H). (Solvent A) |
| 46 | 1.28(t, 3H); 1.56(s, 6H); 2.36(s, 3H); 3.4–4(m, 2H); 3.8–4.3(m, 2H); 4.16(d, 1H); 4.58(d, 1H); 5.16(d, 1H); 5.84(d, 1H); 6.9(s, 1H); 7.08(s, 1H); 7.56(s, 1H). (Solvent A) |
| 47 | 1.50(s, 3H); 1.53(s, 3H); 3.46(d, 1H); 3.63(d, 1H); 4.17 and 4.22(dd, 1H); 4.40 and 4.47(dd, 1H); 5.14(d, 1H); 5.17(d, 1H); 5.80 and 5.83(dd, 1H); |

Solvent A:- (CD$_3$)$_2$SO/CD$_3$COOD/CF$_3$COOD
Solvent B:- (CD$_3$)$_2$SO/CD$_3$COOD
Solvent C:- (CD$_3$)$_2$SO
Solvent D:- (CD$_3$)$_2$SO/CF$_3$COOD

| Example | Delta Values (ppm) |
|---|---|
|  | 6.79(s, 1H); 6.85(s, 1H); 6.89(s, 1H); 7.05(s, 1H); 8.5(t, 1H); 9.68(d, 1H). (Solvent D) |
| 48 | 1.54(s, 6H); 3.77(m, 2H); 4.26(d, 1H); 4.51(d, 1H); 5.19(d, 1H); 5.90(d, 1H); 6.59(s, 1H); 7.04(s, 1H); 7.22(s, 1H); 8.46(s, 1H). (Solvent A) |
| 49 | 1.54(m, 6H); 3.3–3.89(m, 2H); 4.13(d, 1H); 4.54(d, 1H); 5.18(d, 1H); 5.85(d, 1H); 7.07(s, 1H); 7.42(s, 1H); 7.51(s, 1H); 7.72(s, 1H). (Solvent A) |
| 50 | 1.4–1.65(m, 6H); 3.43(d, 1H); 3.7(d, 1H); 4.08(d, 1H); 4.5(d, 1H); 5.13(d, 1H); 5.8(d, 1H); 7.06(s, 2H); 7.31(s, 1H); 7.52(s, 1H). (Solvent A) |
| 51 | 1.49(s, 3H); 1.92(s, 3H); 2.27(s, 3H); 2.33(s, 3H); 3.62(dd, 2H); 4.02(dd, 1H); 4.48(dd, 1H); 5.12(d, 1H): 5.82(dd, 1H); 7.02(s, 1H); 7.39(d, 1H); 7.85(d, 1H); 8.84(s, 1H); 8.95(t, 1H); 9.65(d, 1H). (Solvent D) |
| 52 | 1.48(s, 1H); 1.52(s, 3H); 3.62(dd, 2H); 4.0(dd, 1H); 4.46(dd, 1H); 5.13(d, 1H); 5.82(dd, 1H); 6.86(d, 1H); 7.01(s, 1H); 7.20(d, 1H); 8.69(s, 1H); 9.03(t, 1H); 9.66(d, 1H). (Solvent D) |
| 53 | 1.35(t, 3H); 3.62(dd, 2H); 4.02(dd, 1H); 4.20(q, 2H); 4.48(dd, 1H); 5.13(d, 1H); 5.77(dd, 1H); 6.89(d, 1H); 6.95(s, 1H); 7.25(d, 1H); 8.70(s, 1H); 9.04(t, 1H); 9.80(d, 1H). (Solvent D) |
| 54 | 1.40(bs, 6H); 3.60(dd, 2H); 3.98(d, 1H); 4.47(d, 1H); 5.12(d, 1H); 5.84(d, 1H); 6.72(s, 1H); 6.84(s, 1H); 7.20(s, 1H); 8.72(s, 1H); 9.08(bs, 1H). (Solvent B) |
| 55 | 1.48(s, 3H); 1.51(s, 3H); 3.62(dd, 2H); 4.02(dd, 1H); 4.18(dd, 1H); 5.13(d, 1H); 5.83(dd, 1H); 7.01(s, 1H); 7.62(s, 1H); 8.70(s, 1H); 9.02(t, 1H); 9.77(d, 1H). (Solvent D) |
| 56 | 1.22(t, 3H); 3.62(dd, 2H); 4.02(dd, 1H); 4.20(q, 2H); 4.48(dd, 1H); 5.13(d, 1H); 5.78(dd, 1H); 6.98(s, 1H); 7.65(s, 1H); 8.72(s, 1H); 9.02(t, 1H); 9.68(d, 1H). (Solvent D) |
| 57 | 1.51(s, 3H); 1.54(s, 3H); 2.28(s, 3H); 3.62(dd, 2H); 4.13(dd, 1H); 4.42(dd, 1H); 5.17(d, 1H); 5.83(dd, 1H); 6.82(d, 1H); 7.04(s, 1H): 7.12(d, 1H); 8.65(t, 1H); 9.66(d, 1H). (Solvent D) |
| 58 | 1.48(s, 3H); 1.53(s, 3H); 2.29(s, 3H); 3.60(dd, 2H); 4.12(dd, 1H); 4.42(dd, 1H); 5.16(d, 1H); 5.83(dd, 1H); 7.03(s, 1H); 7.43(s, 1H); 8.70(t, 1H); 9.68(d, 1H). (Solvent D) |
| 59 | 1.34(t, 3H); 1.49(s, 3H); 1.51(s, 3H); 3.6(q, 2H); 4.03(dd, 1H); 4.26(q, 2H); 4.42(dd, 1H); 5.16(d, 1H); 5.84(dd, 1H); 7.03(s, 1H); 7.07(s, 1H): 8.66(s, 1H); 9.67(d, 1H). (Solvent D) |
| 60 | 1.26(t, 3H); 1.36(t, 3H); 3.6(q, 2H); 4.04(dd, 1H); 4.21(q, 2H); 4.31(q, 2H); 4.66(dd, 1H); 5.17(d, 1H); 5.8(dd, 1H); 6.97(s, 1H); 7.08(s, 1H); 8.66(s, 1H); 9.81(d, 1H). (Solvent D) |
| 61 | 1.51(t, 3H); 1.53(t, 3H); 3.66(q, 2H); 4.17(dd, 1H); 4.58(dd, 1H); 5.19(d, 1H); 5.86(dd, 1H); 7.05(s, 1H); 7.52(s, 1H); 7.62(s, 1H); 9.04(s, 1H); 9.68(d, 1H). (Solvent D) |
| 62 | 1.50(t, 3H); 1.53(t, 3H); 2.28(s, 3H); 3.58(q, 2H); 4.16(dd, 1H); 4.63(dd, 1H); 5.17(d, 1H); 5.84(dd, 1H); 6.83(s, 1H); 7.02(s, 1H); 7.40(d, 1H); 7.42(d, 1H); 9.67(d, 1H). (Solvent D) |
| 63 | 1.54(m, 6H); 3.42(s, 3H); 3.3 and 3.9(m, 2H); 4.1(d, 1H); 4.54(d, 1H); 5.15(d, 1H); 5.8(d, 1H); 6.62(s, 1H); 6.94(s, 1H); 7.08(s, 1H); 7.57(s, 1H). (Solvent A) |

PREPARATION OF STARTING MATERIALS

Cephalosporins

Reference may be made to EP-A-127992 and EP-A-164944 for general descriptions of methods suitable for the preparation of cephalosporin starting materials. The starting materials for the Examples of the present invention including:

3-aminomethyl-7-[2-(2-aminothiazol-4-yl)-2-((Z)-1-carboxy-1-methylethoxyimino)acetamido]ceph-3-em-4-carboxylic acid;

3-aminomethyl-7-[2-(2-aminothiazol-4-yl)-2-((Z)-1-ethoxyimino)acetamido]ceph-3-em-4-carboxylic acid; and 3-ethylaminomethyl-7-[2-(2-aminothiazol-4-yl)-2-((Z)-1-ethoxyimino)acetamido]ceph-3-em-4-carboxylic acid;

are specifically described in EP-A-164944.

Preparation of heterocyclic carbonyl chlorides or activated esters.

The carbonyl chlorides (for reacting with the 3-aminomethyl cephalosporins) are prepared in conventional manner from the corresponding acids. Examples of conventional methods include dissolving the corresponding acid in anhydrous dichloromethane with thionyl chloride (at least one equivalent) and stirring for 1–3 hours at room temperature. In certain Examples the heterocyclic acid is dissolved in dichloromethane in the presence of trimethylsilylchloride and triethylamine (e.g. Examples 4–14, 16, 17 and 59).

In Example 15, the heterocycle (306 mg) was heated at reflux for 2.5 hours with hexamethyldisilazane (1.26 ml) and saccharin (20 mg) in chloroform (10 ml). The reaction mixture was evaporated under reduced pressure and then converted to the acid chloride as described above.

In Examples 45, 51–58, the heterocyclic acid was converted to the corresponding acid chloride with PCl$_5$ in dichloromethane at a temperature in the range 20°–40° C. for up to 2 hours. The solvents were evaporated and the residue triturated in toluene to give the solid acid chloride.

The activated esters (for reacting with the 3-aminomethylcephalosporins) are prepared in conventional manner from the corresponding acid. Examples of conventional methods include dissolving the corresponding acid in dimethylformamide, adding triethylamine (1 equivalent), o-hydroxybenzotriazole and dicyclohexylcarbodi-imide; stirring for about 90 minutes and filtering (to remove urea).

The carbonyl chloride and activated esters were reacted with the appropriate cephalosporin without further purification.

Preparation of Heterocyclic carboxylic acids

The heterocyclic carboxylic acids (for preparing the carbonyl chlorides or activated esters) are known or are prepared as described below:

| ACID HOOC—X USED FOR PREPARATION OF CHLORIDE/ESTER OF EXAMPLE | COMMENTS |
|---|---|
| [Structure: 1-Et quinolone with 6,7-di(OCOCH$_2$Ph)] 1,2,3,4 | Prepared by BBr$_3$ cleavage, at 15 hours (no solvents), of the corresponding 6,7-methylenedioxy compound to form the catechol. Followed by acylation with phenylacetyl chloride and diazabicycloundecene (DBU) in acetonitrile. NMR (CDCl$_3$) 1.54(t, 3H); 3.56 and 3.68(2s, 4H); 4.27(q, 2H); 7.35(s, 10H); 7.52 and 8.28(2s, 2H); 8.73(s, 1H). |
| [Structure: 1-Me quinolone with 6,7-di(OH)] 5 | Prepared by BBR$_3$ (2.5 ml) cleavage of the corresponding 6,7-methenedioxy compound (312 mg) at room temperature for 4 hours in a suspension in dichloromethane (5 ml), followed by evaporation, pouring on to iced water and chromatography (eluting with 0.2% ammonia) to give 1,4-dihydro-6,7-dihydroxy-1-methyl-4-oxoquinoline-3-carboxylic acid. NMR (DMSO-d$_6$/CF$_3$COOD 3.98(s, 3H); 7.18, 7.63 and 8.80(3s, 3H). |
| [Structure: 1-Bu$^n$ quinolone with 6,7-di(OH)] 6 | 1,4-Dihydro-6,7-dihydroxy-4-oxoquinoline-3-carboxylic acid (1.32 g) in dichloromethane (60 ml) was treated with bis silylacetamide (7 ml) for 2 hours, the solvents were evaporated and the residue in dimethylformamide (30 ml) was treated with sodium hydride (0.315 g), the anion was formed by heating for 30 minutes and n-butyl iodide (0.725 ml) was added. The reaction mixture was stirred overnight at room temperature, evaporated and purified by chromatography to give 1,4-dihydro-6,7-dihydroxy-1-n-butyl-4-oxoquinoline-3-carboxylic acid. |
| [Structure: 1-CH$_2$CH=CH$_2$ quinolone with 6,7-di(OH)] 7 | Ethyl 1,4-dihydro-6,7-methlenedioxy-4-oxo-quinoline-3-carboxylate (1.56 g) in dimethylformamide (30 ml) was treated with sodium hydride (0.316 g) and allylbromide (1.1 eq) at 70° C. Purification by chromatography gave the 1-allyl compound. The ethyl group was removed with ethanolic KOH and the dioxy group cleaved with BBr$_3$ as in Example 1 to give 1,4-dihydro-6,7-dihydroxy-1-allyl-4-oxoquinoline-3-carboxylic acid. NMR (DMSO-d$_6$) 5.2(m, 4H); 6.08(m, 1H); 7.0 and 7.56(2s, 2H); 8.76(s, 1H). |
| [Structure: 1-CH$_2$CH$_2$NHCOOBu$^t$ quinolone with 6,7-di(OH)] 8 | As for 6 above, except that the alkylation was performed with t-butoxycarbonylaminoethyl iodide to give 1,4-dihydro-6,7-dihydroxy-1-t-butoxycarbonylamino ethyl-4-oxoquinoline-3-carboxylic acid. NMR (DMSO-d$_6$/CF$_3$COOD) 1.22(s, 9H); 3.25–3.5(m, 2H); 4.3–4.55(m, 2H); 8.68, 7.67, 7.28(3s, 3H). |
| [Structure: 1-Et quinolone with 6,7-di(OH)] 9 | 1,4-Dihydro-6,7-dihydroxy-1-ethyl-4-oxoquinoline-3-carboxylic acid was prepared as in the first part of 1 above. NMR (DMSO-d$_6$) 1.42(t, 3H); 4.46(q, 3H); 7.23(s, 1H); 7.66(s, 1H); 8.82(s, 1H). |

-continued

ACID

HOOC—X

USED FOR PREPARATION

OF CHLORIDE/ESTER OF

| EXAMPLE | COMMENTS |
|---|---|
| 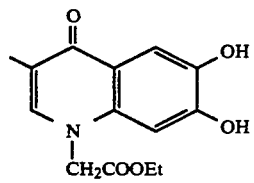<br>10 | As for 6 above, except that the alkylation was performed with ethoxycarbonylmethyl iodide to give 1,4-dihydro-6,7-dihydroxy-1-ethoxycarbonylmethyl-4-oxoquinoline-3-carboxylic acid.<br>NMR (DMSO-$d_6$/CF$_3$COOD) 1.23(t, 3H); 4.21(q, 2H); 5.39(s, 2H); 6.96, 7.67, 8.87(3s, 3H). |
| 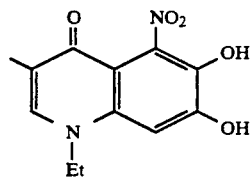<br>11,12 | The corresponding 6,7-methylenedioxy compound (900 mg) (Frank et al., European Journal of Medicinal Chemistry, 1979, 14, 61) in 2N NaOH (30 ml) at 60° C., followed by cooling and acidification to pH1 gave a precipitate of 1,4-dihydro-6,7-dihydroxy-1-ethyl-5-nitro-4-oxoquinoline-3-carboxylic acid.<br>NMR (DMSO-$d_6$/CF$_3$COOD) 1.15(t, 3H); 4.15(q, 2H); 7.0(s, 1H); 8.5(s, 1H). |
| <br>13 | As for 6 above, except that alkylation was performed with NH$_2$COCH$_2$I to give 1,4-dihydro-6,7-dihydroxy-1-carbonylmethyl-4-oxoquinoline-3-carboxylic acid.<br>NMR (DMSO-$d_6$/CF$_3$COOD) 5.10(s, 2H); 6.97(s, 1H); 7.67(s, 1H); 8.80(s, 1H). |
| 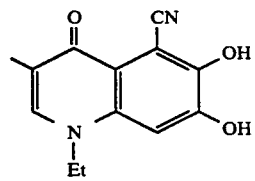<br>14 | The corresponding 5-amino-6,7-methylenedioxy compound (2.76 g) was treated with nitrosyl sulphuric acid (ONOSO$_3$H) (1.9 g) in acetic acid (20 ml) to give the diazonium sulphate (3.7 g) as a precipitate. This was dried and added in portions to NaCu(CN)$_2$ (1.75 g of NaCN and 1.6 g CuCN) in water (1 ml) to give, after 2 hours, a precipitate. This was collected and acidified with 2N HCl to give the 5-cyano compound (1.2 g). This was cleaved with BBr$_3$ (20 ml) at reflux for 24 hours to give, after chromatography, 1,4-dihydro-6,7-dihydroxy-1-ethyl-5-cyano-4-oxoquinoline-3-carboxylic acid.<br>NMR (DMSO-$d_6$/CF$_3$COOD) 1.3–1.6(m, 3H); 4.3–4.65(m, 2H); 7.45(s, 1H); 8.9(s, 1H). |
| 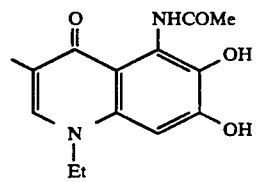<br>15 | The corresponding 6,7-methylenedioxy compound (1 g) (Frank et al) in BBr$_3$ and CH$_2$Cl$_2$ (5 ml) at room temperature for 16 hours gave, after evaporation, hydrolysis and chromatography, 1,4-dihydro-6,7-dihydroxy-1-ethyl-5-acetamido-4-oxoquinoline-3-carboxylic acid.<br>NMR (DMSO-$d_6$/CF$_3$COOD) 1.25–1.6(m, 3H); 2.25(s, 3H); 4.25–4.6(m, 2 H); 7.15(s, 1H); 8.85(s, 1H). |

-continued

ACID

HOOC—X

USED FOR PREPARATION
OF CHLORIDE/ESTER OF

| EXAMPLE | COMMENTS |
|---|---|
| 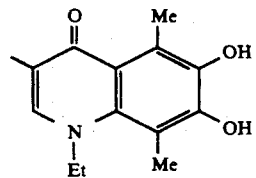<br>16 | 2,3-Dihydroxy-1,4-dimethylphenol (Sinhahatu et al., Synth. Comm., 1982, 12, 983) was protected as the dimethoxy compound; mononitrated with fuming nitric acid; hydrogenated to give the 5-amino compound and reductively alkylated with acetaldehyde and NaBH$_3$CN to give the 5-ethylamino compound. This was reacted with ethoxymethylene malonate in polyphosphoric esters at 120°° C. to give ethyl 6,7-dimethoxy-5,8-dimethyl-1-ethyl-4-oxo-quinoline-3-carboxylate. The ethyl group was cleaved with ethanolic NaOH and the methoxy group cleaved with BBr$_3$/CH$_2$Cl$_2$ at reflux to give 1,4-dihydro-6,7-dihydroxy-5,8-dimethyl-1-ethyl-4-oxoquinoline-3-carboxylic acid.<br>NMR (DMSO-d$_6$/CD$_3$COOD/CF$_3$COOD) 1.2(t, 3H); 2.4(s, 3H); 2.7(s, 3H); 4.5(q, 2H); 8.7(s, 1H). |
| 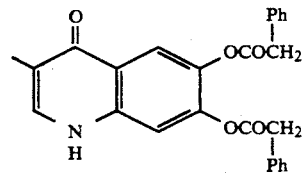<br>17 | Prepared analogously to Example 1 above. This was acylated with phenylacetyl chloride and triethylamine in acetonitrile. 1,4-dihydro-6,7-methylenedioxy-4-oxoquinoline-3-carboxylic acid (7.7 g) was added to BBr$_3$ (33 ml). The mixture was stirred for 48 hours at room temperature, heated at 70° C. for 24 hours to complete deprotection, added at 0° C. to water to give a precipitate which was purified by chromatography (aqueous methanol; product removed from column by 0.2% ammonia) to give 1,4-dihydro-6,7-dihydroxy-4-oxoquinoline-3-carboxylic acid.<br>NMR (DMSO-d$_6$) 7.07(s, 1H); 7.51(s, 1H); 8.6(s, 1H). This was acylated with phenylacetyl chloride and triethylamine in acetonitrile. |
| 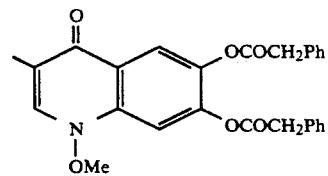<br>18 | The corresponding 6,7-methylenedioxy compound was cleaved with BBr$_3$/CH$_2$Cl$_2$; followed by acylation with phenylacetyl chloride and DBU to give 1,4-dihydro-6,7-diphenylacetoxy-1-methoxy-4-oxoquinolinde-3-carboxylic acid.<br>NMR (CDCl$_3$) 3.56(s, 2H); 3.66(s, 2H); 4.18(s, 3H); 7.2–7.3(m, 10H); 7.64(s, 1H); 8.22(s, 1H); 8.92(s, 1H). |
| 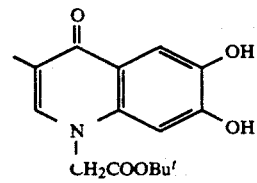<br>19 | As for 6 above, except that alkylation was performed with t-butyl bromoacetate to give 1,4-dihydro-6,7-dihydroxy-1-t-butoxycarbonylmethyl-4-oxoquinoline-3-carboxylic acid.<br>NMR (DMSO-d$_6$) 1.44(s, 9H); 5.02(s, 1H); 5.96(s, 1H); 8.46(s, 1H). |
| 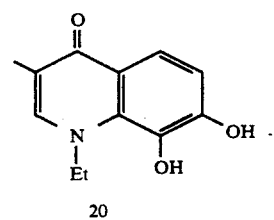<br>20 | 2,3-Dimethoxyaniline (0.75 g) in ethanol (20 ml) was treated, at reflux, with Raney nickel (0.3 g) to give after chromatography N-ethyl-1-2,3-dimethoxyaniline (0.52 g). This was reacted with diethylethoxymalonate (1 eq) at 140° C. for 7 hours, the product was purified and subsequently heated at reflux for 90 minutes with phosphorus oxychloride to give after evaporation, dissolution in water and KI treatment ethyl 1,4-dihydro-7,8-dimethoxy-1- |

| ACID HOOC—X USED FOR PREPARATION OF CHLORIDE/ESTER OF EXAMPLE | COMMENTS |
|---|---|
| | ethyl-4-oxo-quinoline-3-carboxylate. The ethyl group was cleaved with 48% HBr at reflux (also cleavage of at least one methoxy group) and BBr₃ treatment at room temperature for 5 hours followed by hydrolysis in iced water and acidification of the resulting precipitate gave 1,4-dihydro-7,8-dihydroxy-1-ethyl-4-oxoquinoline-3-carboxylic acid. NMR (DMSO-d₆) 1.4(t, 3H); 4.82(q, 2H); 7.23(d, 1H); 7.82(d, 1H); 8.76(s, 1H); 10.9(s, 1H). |
| 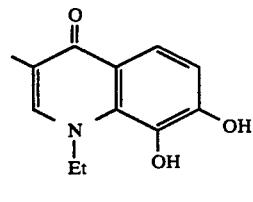 21 | 6,7-Dimethoxy-4-oxoquinolin-2-carboxylic acid (2.5 g) (Biefert et al., Chem Ber, 93, 634 (1960) in benzene (100 ml) containing bis trimethylsilylacetamide (20 ml) (having been heated to give a solution) was cleaved by the addition of BBr₃ with subsequent heating to 60° C. Evaporation, hydrolysis and collection of the precipitate gave 1,4-dihydro-6,7-dihydroxy-4-oxoquinoline-2-carboxylic acid. NMR (DMSO-d₆) 6.6(s, 1H); 7.35(s, 1H); 7.4(s, 1H). |
| 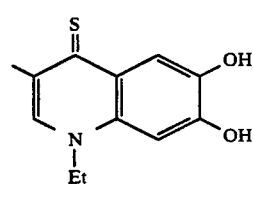 22 | The corresponding 6,7-methylenedioxy compound in the form of the ethyl carboxylate was cleaved with BBr₃; subsequent treatment with sodium hydrosulphide in water followed by acidification to pH2 gave 1,4-dihydro-6,7-dihydroxy-1-ethyl-4-thioxoquinoline-3-carboxylic acid. NMR (DMSO-d) 1.42(t, 3H); 4.53(q, 2H); 7.22(s, 1H); 8.24(s, 1H); 8.97(s, 1H). This was acylated with acetic anhydride and pyridine to provide the diacetoxy compound NMR (DMSO-d₆) 1.42(t, 3H); 2.38(s, 6H); 4.62(q, 2H); 8.17(s, 1H); 8.71(s, 1H); 9.19(s, 1H). |
| 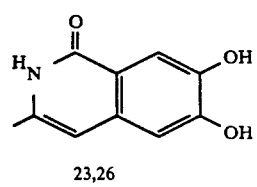 23,26 | The corresponding dimethoxy compound (0.45 g) was cleaved with BBr₃ (1.5 ml) in dichloromethane (4 ml) at 40° C. for 30 minutes. Evaporation, treatment with ice, 2N NaOH and 6N HCl gave as a solid, 1,2-dihydro-6,7-dihydroxy-1-oxo-isoquinoline-3-carboxylic acid. NMR (DMSO-d₆/CF₃COOD) 7.13(s, 1H); 7.23(s, 1H); 7.6(s, 1H). |
| 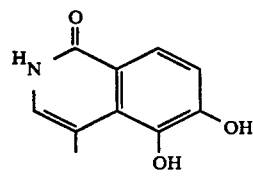 24 | The corresponding N-methyl dimethoxy compound (0.25 g) was cleaved and demethylated with BBr₃ at 50° C. for 3 hours to give, after work-up, 1,2-dihydro-6,7-dihydroxy-1-oxo-isoquinoline-4-carboxylic acid. NMR (DMSO-d₆/CF₃COOD) 6.65(d, 1H); 7.61(d, 1H); 9.63(s, 1H). |
| 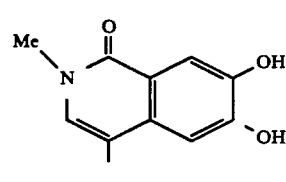 25 | The corresponding dimethoxy compound (0.46 g) was cleaved with BBr₃ (3 ml) at 50° C. for 90 minutes. Evaporation, treatment with ice and chromatography (0.5% ammonia) gave 1,2-dihydro-6,7-dihydroxy-2-methyl-1-oxo-isoquinoline-4-carboxylic acid. NMR (DMSO-d₆/CF₃COOD) 3.52(s, 3H); 7.61(s, 1H); 8.16(s, 1H); 8.23(s, 1H). |
| 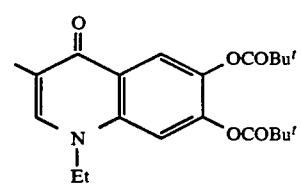 27 | The starting material for 9 above (2 g) with triethylamine (3.34 ml) in dichloromethane was acylated with pivaloyl chloride (2 ml) to give 1,4-dihydro-6,7-dipivaloyloxy-1-ethyl-4-oxoquinoline-3-carboxylic acid. NMR (DMSO-d₆/CD₃COOD) 1.25–1.6(m, 21H); 4.4–4.75(m, 2H); 7.98(s, 1H); 8.18(s, 1H); 9.04(s, 1H). |

-continued

| ACID HOOC—X USED FOR PREPARATION OF CHLORIDE/ESTER OF EXAMPLE | COMMENTS |
|---|---|
| 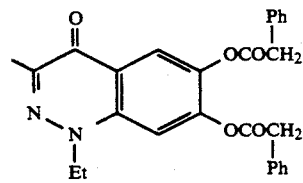<br>28,29 | 1-Ethyl-6,7-methylenedioxy-4-oxocinnoline-3-carboxylic acid (6.5 g) was cleaved with BBr$_3$ (20 ml) by stirring at room temperature for 16 hours followed by 80° C. for 1 hour with subsequent cooling, hydrolysis and chromatography to give 1,4-dihydro-6,7-dihydroxy-1-ethyl-4-oxocinnoline-3-carboxylic acid.<br>NMR (D$_2$O+NaOD) 1.37(t, 3H); 4.4(q, 2H); 6.52(s, 1H); 6.9(s, 1H);<br>This was suspended in acetonitrile and acylated with phenylacetyl chloride and DBU to give the diphenylacetoxy compound.<br>NMR (DMSO-d$_6$/CF$_3$COOD/CD$_3$COOD) 1.46(t, 3H); 3.84 and 3.89(2s, 4H); 3.7(q, 2H); 8.18 and 8.2(2s, 2H). |
| 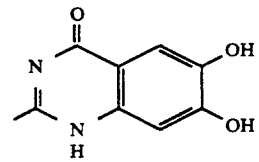<br>30 | 2-Amino-4,5-dimethoxybenzamide (0.197 g) and ethyl oxalate (0.3 g) at 160° C. for 1 hour gave, after trituration, ethyl 1,4-dihydro-6,7-dimethoxy-4-oxoquinazoline-3-carboxylate (0.2 g).<br>NMR (DMSO-d$_6$) 1.35(t, 3H); 3.8(s, 6H); 4.3(q, 2H); 7.45(s, 1H); 8.3(s, 1H).<br>Cleavage of the ethyl group with 2N NaOH (50 ml), followed by BBr$_3$ (20 eqs) in benzene (100 ml) (in the presence of bis trimethylsilylacetamide (6 eqs) gave, after evaporation and hydrolysis, 1,4-dihydro-6,7-dihydroxy-4-oxoquinazoline-2-carboxylic acid.<br>NMR (DMSO-d$_6$/CF$_3$COOD) 7.15(s, 1H); 7.45(s, 1H); [contaminated with dicarboxylated pyrimidine]. |
| 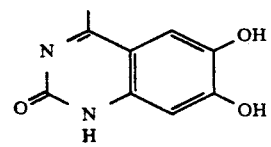<br>31 | 5,6-Dimethoxyisatin (2.07 g) and KOH (0.56 g) in water (4 ml) gave potassium 2-amino-4,5-dimethoxyphenyloxalate (2.2 g). This was treated with urethane at 140° C. for 6 hours, cooled and triturated under ether to give a potassium salt which was acidified to provide the 6,7-dimethoxy quinazoline. This was treated with BBr$_3$ in benzene (in the presence of bistrimethyl silylacetamide) as in 30 above to give 1,2-dihydro-6,7-dihydroxy-2-oxoquinazoline-4-carboxylic acid.<br>NMR (DMSO-d$_6$/CF$_3$COOD) 6.8(s, 1H); 7.5(s, 1H). |
| 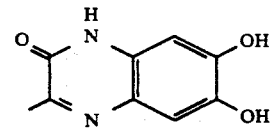<br>32,33 | The corresponding 6,7-methylenedioxy compound (10 g) was cleaved with BBr$_3$ (150 ml) at 50° C. for 9 hours. Cooling, evaporation, hydrolysis and chromatography gave after acidification at pH2 1,2-dihydro-6,7-dihydroxy-3-oxoquinoxaline-2-carboxylic acid.<br>NMR (DMSO-d$_6$/CF$_3$COOD/CD$_3$COOD) 6.88(s, 1H); 7.23(- 1H). |
| 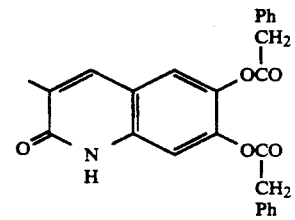<br>34 | Prepared from the corresponding catechol by acylation with phenylacetyl chloride and DBU to give the diphenylacetoxy compound.<br>NMR (DMSO-d$_6$) 3.92(s, 4H); 7.33(s, 10H, 7.38(s, 1H); 7.95(s, 1H); 8,86(s, 1H); 13.2(br s, 1H); 14.5(br s, 1H). |

| ACID HOOC—X USED FOR PREPARATION OF CHLORIDE/ESTER OF EXAMPLE | COMMENTS |
|---|---|
| 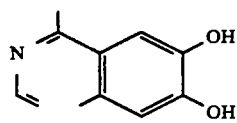<br>35 | Potassium 2-amino-4,5-dimethoxyphenyloxalate (2.3 g) (see 31 above) was added to sodium formate (6.4 g) and formic acetic anhydride (13 ml) to give N-formyl 5,6-diamethoxyisatin (4.6 g). This was precipitated with methanol and the precipitate treated with aqueous KOH to provide, after lyophilisation, potassium 2-formylamino-4,5-dimethoxyphenyloxalate (1.2 g), which was heated, in a pressure vessel at 130° C. for 9 hours, in methanolic ammonia (40 ml). The mixture was cooled, the crystals collected and acidified to pH2 in water to give 6,7-dimethoxyquinazoline-4-carboxylic acid. This was deprotected as in 30 above to afford 6,7-dihydroxyquinazoline-4-carboxylic acid. NMR (DMSO-$d_6$) 7.28(s, 1H); 7.77(s, 1H); 9.02(s, 1H). |
| 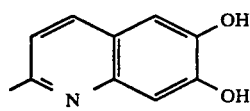<br>36 | 6,7-Dimethoxyquinoline-2-carboxylic acid (1 g) (Borsche et al., Ann (1943), 269, 554) in benzene (200 ml) was deprotected as in 30 above to give 6,7-dihydroxyquinoline-2-carboxylic acid. NMR (DMSO-$d_6$/CF$_3$COOD) 7.5(s, 1H); 7.9(s, 1H); 8.1(d, 1H); 8.8(d, 1H). |
| 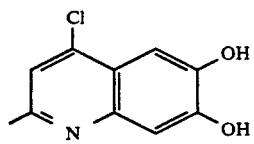<br>37 | Ethyl 6,7-dimethoxyquinoline-2-carboxylate (2.8 g) was stirred with phosphorous oxychloride (10 ml) at reflux for 1 hour to give, after work-up, the corresponding 4-chloro compound. This was treated with ethanolic NaOH at reflux for 2 hours and deprotected as in 30 above to provide 4-chloro-6,7-dihydroxyquinoline-2-carboxylic acid. NMR (DMSO-$d_6$/CF$_3$COOD) 7.58(s, 1H) ; 7.83(s, 1H); 8.16(s, 1H). |
| 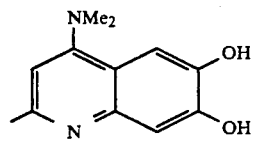<br>38 | Ethyl 4-chloro-6,7-dimethoxyquinoline-2-carboxylate (1.5 g) (37 above) was heated, in a pressure vessel at 150° C. for 2 hours, with dimethylamine (10 ml) and dimethylformamide (25 ml). Evaporation and chromatography gave the purified corresponding 4-dimethylamino compound. This was treated with ethanolic NaOH (0.81 g) for 90 minutes and subsequently BBr$_3$ (as in 30 above) to give 4-dimethylamino-6,7-dihydroxyquinoline-2-carboxylic acid (DMSO-$d_6$/CF$_3$COOD) 3.40(s, 6H); 7.2(s, 1H); 7.64(s, 2H). |
| 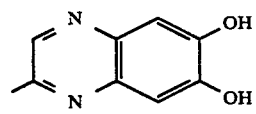<br>39 | 6,7-Dimethoxyquinoxaline-2-carboxylic acid was heated in hydrobromic acid at 100° C. for 7 hours. Cooling and evaporation gave 6,7-dihydroxyquinoxaline-2-carboxylic acid. NMR (DMSO-$d_6$/CF$_3$COOD/CD$_3$COOD) 7.34(s, 1H); 7.38(s, 1H); 9.1(s, 1H). |
| 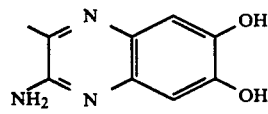<br>40 | 6,7-Dimethoxy-2-aminoquinoxaline-3-carboxylic acid (1.5 g) in BBr$_3$ (20 ml) at 50° C. for 24 hours, followed by evaporation, treatment with ice and chromatography (0.5% ammonia) of the resultant solid gave, after acidification, 6,7-dihydro-2-aminoquinoxaline-3-carboxylic acid. NMR (DMSO-$d_6$/CF$_3$COOD/CD$_3$COOD) 7.1(s, 1H); 7.3(s, 1H). |

-continued

| ACID HOOC—X USED FOR PREPARATION OF CHLORIDE/ESTER OF EXAMPLE | COMMENTS |
|---|---|
| 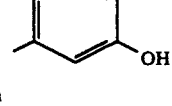<br>41 | 6,7-Dimethoxy-2-benzylaminoquinoxaline-3-carboxylic acid (1.2 g) in BBr$_3$ (10 ml) and CH$_2$Cl$_2$ (10 ml) at 40° C. for 4 hours gave after work-up as in 40 above, 6,7-dihydro-2-benzylaminoquinoxaline-3-carboxylic acid. NMR (DMSO-d$_6$/CF$_3$COOD/CD$_3$COOD) 4.8(s, 2H); 7.15-7.5(m, 1H). |
| 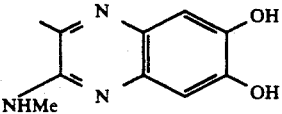<br>42 | 6,7-Dimethoxy-2-methylaminoquinoxaline-3-carboxylic acid in BBr$_3$ at 50° C. as in 40 above gave 6,7-dihydro-2-methylaminoquinoxaline-3-carboxylic acid. NMR (DMSO-d$_6$/CF$_3$COOD/CD$_3$COOD) 3.17(s, 3H); 7.3(s, 1H); 7.35(s, 1H). NMR (DMSO-d$_6$/CF$_3$COOD/CD$_3$COOD). |
| 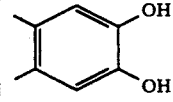<br>(X = Br, Cl)<br>43 | 6,7-Dimethoxy-2-chloroquinoxaline-3-carboxylic acid (0.35 g) was heated at reflux with BBr$_3$ (3 ml) and CH$_2$Cl$_2$ (3 ml). The mixture was evaporated, dissolved at pH 10 with NaOH and then acidified to pH1 with HCl to give a 50:50 mixture of 2-chloro and 2-bromo 6,7-dihydroxy quinoxaline-3-carboxylic acid. NMR (DMSO-d$_6$/CF$_3$COOD/CD$_3$COOD) 7.24(s, 1H); 7.30(s, 1H); 7.32(s, 1H). |
| 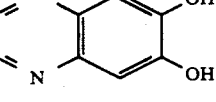<br>44 | 6,7-Dimethoxyquinoxaline-2,3-dicarboxylic acid (1.2 g) was heated at 60° C. for 12 hours in BBr$_3$ (25 ml) and CH$_2$Cl$_2$ (15 ml). Work-up as in 40 above (chromatography using aqueous methanol containing 1% acetic acid) gave 6,7-dihydroxyquinoxaline-2,3-dicarboxylic acid. NMR (DMSO-d$_6$/CF$_3$COOD) 7.35(s, 2H). |
| 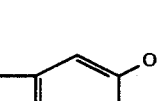<br>45 | 6,7-Dihydroxyquinoxaline-2,3-dicarboxylic acid (0.5 g) (from 44 above) was heated at reflux with acetic anhydride (25 ml) for 30 minutes. The solvent was evaporated and the residue heated in methanol (20 ml) to give, after evaporation, 6,7-diacetoxyquinoxaline-2-methoxycarbonyl-3-carboxylic acid (0.57 g). NMR (DMSO-d$_6$/CF$_3$COOD) 2.38(s, 6H); 2.96(s, 3H); 8.17(s, 2H). |
| <br>46 | 2-Ethoxycarbonyl-5,6-dimethoxyindole (1.36 g) in acetyl chloride (20 ml) with zinc chloride (0.53 g) at room temperature for 12 hours followed by 50° C. for 2 hours afforded the corresponding 3-acetylindole after chromatography. This was treated with sodium hydride (0.42 g) and ethyl iodide (680 μl) in dimethylformamide (20 ml) to give the N-ethyl compound after chromatography. Methanolic KOH and subsequently cleavage with BBr$_3$ (3.6 ml) in CH$_2$Cl$_2$ (40 ml), followed by evaporation hydrolysis and chromatography provided 3-acetyl-1-ethyl-5,6-dimethoxyindole-2-carboxylic acid. NMR (DMSO-d$_6$/CF$_3$COOD) 1.3(t, 3H); 2.5(s, 3H); 4.3(q, 2H); 6.92(s, 1H); 7.39(s, 1H). |
| <br>47 | 5,6-Dihydroxyindole-2-carboxylic acid. |

| ACID HOOC—X USED FOR PREPARATION OF CHLORIDE/ESTER OF EXAMPLE | COMMENTS |
|---|---|
| 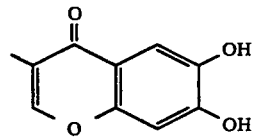<br>48 | 6,7-Diacetoxy-4-oxo-4H-1-benzopyran-3-carboxylic acid (Tetrahedron Letters 1973, 1995). |
| 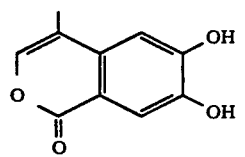<br>49 | The corresponding 6,7-dimethoxy compound (0.68 g) was stirred at 20° C. for 3 hours in BBr$_3$ (5 ml) and CH$_2$Cl$_2$ (5 ml), evaporated and treated with ice, to give as a solid, 6,7-dihydroxyisocoumarin-4-carboxylic acid. NMR (DMSO-d$_6$/CF$_3$COOD) 7.52(s, 1H); 8.08(s, 1H); 8.14(s, 1H). |
| 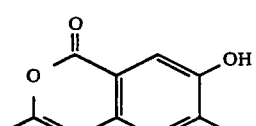<br>50 | The corresponding 6,7-dimethoxy compound (0.3 g) was stirred at 20° C. for 3 hours in BBr$_3$ (1.5 ml) and CH$_2$Cl$_2$ (3 ml), evaporated and treated with ice, and dissolved in 1N NaOH and acidified to pH1, to give as a solid, 6,7-dihydroxyisocoumarin-3-carboxylic acid. NMR (DMSO-d$_6$/CF$_3$COOD) 7.11(s, 1H); 7.45(s, 1H); 7.54(s, 1H). |
| 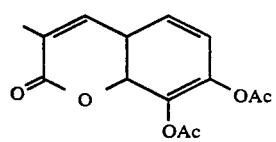<br>51,52,53 | 7,8-Diacetoxycoumarin-3-carboxylic acid. |
| 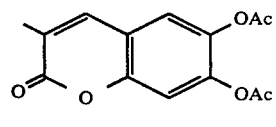<br>54 | 6,7-Diacetoxycoumarin-3-carboxylic acid. |
| 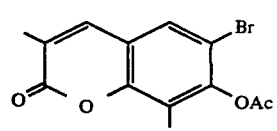<br>55,56 | 5-Bromo-2-hydroxy-3,4-dimethoxybenzaldehyde (0.065 M) and diethylmalonate (1.1 eq) were stirred at reflux in ethanol (60 ml) for 150 minutes at room temperature (and left overnight) in the presence of small amounts of acetic acid (0.2 ml) and piperidine (0.006 M) to give as a precipitate, ethyl 6-bromo-7,8-dimethoxy-2-oxo-2H-benzopyran-3-carboxylate m.p. 138–140° C.<br>This was cleaved with BBr$_3$ (40 ml) in CH$_2$Cl$_2$ for 16 hours, hydrolysed and acidified to give 6-bromo-7,8-dihydroxy-2-oxo-2H-1-benzopyran-3-carboxylic acid (m.p. 248–51° C.) which was acetylated with acetic anhydride to give the corresponding 7,8-diacetoxy compound, m.p. 214–8° C. NMR (DMSO-d$_6$) 2.62(s, 6H); 8.24(s, 1H); 8.68(s, 1H); 13.46(br s, 1H). |
| 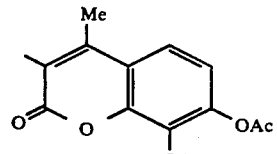<br>57 | 3,4-Dimethoxy-2-hydroxyacetophenone (0.5 M), ethyl cyanoacetate (0.75 M) and sodium ethoxide (0.325 g) was stirred at reflux in ethanol (60 ml). On cooling 4-methoxy-7,8-dimethoxy-3-cyano-2-oxo-1-benzopyran (mp. 221–3° C.) was obtained as a precipitate. This (0.015 M) was heated for 1 hour at 80° C. in concentrated sulphuric acid (25 ml) (with fuming H$_2$SO$_4$ (0.5 ml)) to provide the corresponding 8-hydroxy-7-methoxy-3-carbamoyl compound (m.p. 284° C.). The |

| ACID HOOC—X USED FOR PREPARATION OF CHLORIDE/ESTER OF EXAMPLE | COMMENTS |
|---|---|
| | carbamoyl group was hydrolysed with aqueous NaOH at reflux; BBr$_3$ was added to demethylate and the hydroxy groups were acetylated (as in 55) to give 7,8-diacetoxy-4-methyl-2-oxo-2H-1-benzopyran-3-carboxylic acid, m.p. 124–7° C. NMR (DMSO-d$_6$) 2.35(s, 3H); 2.41(s, 3H); 2.44(s, 3H); 7.35(d, 1H); 7.80(d, 1H). |
| 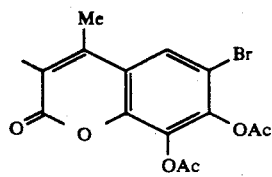<br>58 | 6-Bromo-7,8-dimethoxy-2-oxo-2H-1-benzopyran-3-carboxylic acid (0.027 M) (from 55 above) was treated with PCl$_5$ (0.03 M) in dichloromethane (190 ml) at reflux for 1 hour. Evaporation gave the acid chloride which was added to 35% ammonia (50 ml) at 5–10° C. After stirring for 30 minutes 6-bromo-7,8-dimethoxy-2-oxo-2H-1-benzopyran-3-carboxamide, mp 193–5° C. was collected by filtration. Treatment with trifluoroacetic anhydride/pyridine in dioxan gave the 3-cyano compound (mp 211° C.) which was methylated with diazomethane in ether (Monatsch Chemie (1970), 101, 1123) to give 6-bromo-3-cyano-7,8-dimethoxy-4-methyl-2-oxo-2H-1-benzopyran, mp. 176° C. Treatment with conc H$_2$SO$_4$ (as in 57 above) gave the corresponding 3-carboxamido-7,8-dihydroxy compound mp. 214–8° C. The hydroxy groups were protected by methylation (CH$_3$I/K$_2$CO$_3$) to give the dimethoxy compound (mp 192° C.); the carboxamide group converted to give the carboxylic acid mp. 166° C. (aqueous NaOH, reflux), BBr$_3$ was added to demethylate to afford 6-bromo-7,8-dihydroxy-4-methyl-2-oxo-2H-1-benzopyran-3-carboxylic acid, mp. 185° C. and this compound was acetylated (as in 55) to give 6-bromo-7,8-diacetoxy-4-methyl-2-oxo-2H-1-benzopyran-3-carboxylic acid, m.p. 172–6° C. NMR (CD$_3$CN) 2.35(s, 6H); 2.52(s, 3H); 8.05(s, 1H). |
| 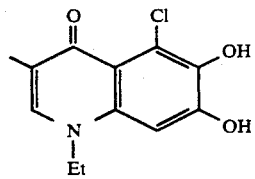<br>59,60 | 1,4-Dihydro-1-ethyl-5-chloro-6,7-dihydroxy-4-oxoquinoline-3-carboxylic acid (J. Het. Chem 18, 985 (1981). |
| 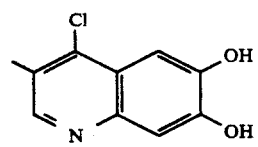<br>61 | 1,1-Diethyl-2-(3,4-dimethoxyanilino)ethylene dicarboxylate (10 g) and POCl$_3$ (50 ml) were heated at reflux for 5 hours, cooled, evaporated, triturated and crystallised to give 4-chloro-6,7-dimethoxy-3-ethoxycarbonylquinoline, BBr$_3$ treatment in dichloromethane at −50° C. rising to 15° C. followed by acid hydrolysis afforded 4-chloro-6,7-dihydroxy quinoline-3-carboxylic acid. NMR (DMSO-d$_6$) 7.30(s, 1H); 7.50(s, 1H); 8.80(s, 1H); 10.44(s, 1H); 10.58(s, 1H). |
| 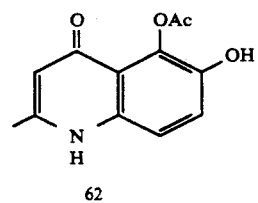<br>62 | 3,4-Diacetoxyaniline (3.98 g) and dimethyl acetylenedicarboxylate (3.32 g) in methanol (120 ml) at room temperature overnight gave, after chromatography, 1,2-dimethoxycarbonyl-1-(3,4-diacetoxy)anilinoethylene. This, (2.7 g) in dichloromethane (15 ml) was added dropwise to diphenyl ether (35 ml) at 80° C. and the resultant solution was heated to 220–230° C. for 90 minutes. Cooling and the addition of hexane gave, after |

-continued

| ACID HOOC—X USED FOR PREPARATION OF CHLORIDE/ESTER OF EXAMPLE | COMMENTS |
|---|---|
| | chromatography, 1,4-dihydro-5,6-diacetoxy-2-methoxycarbonyl-4-oxo-quinoline and its 6,7-diacetoxy isomer. The 5,6-isomer was heated with trimethylsilyl iodide at 106° C. for 2 hours, cooled, diluted with water, taken to pH8, subjected to chromatography (CH$_3$CN/H$_2$O) to give 1,4-dihydro-5-acetoxy-6-hydroxy-4-oxo-quinoline-2-carboxylic acid. NMR (DMSO-d$_6$) 2.27(s, 3H); 6.59(s, 1H); 7.38(s, 2H). |
| 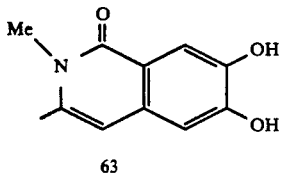 63 | 6,7-Dimethoxy-isocoumarin-3-carboxylic acid (0.6 g) was heated at 100° C. for 2 hours in aqueous methylamine (40%) (60 ml). The mixture was cooled, taken to pH1 and the N-methylisoquinoline collected as a precipitate. This was deprotected with BBr$_3$ (4 ml) in CH$_2$Cl$_2$ (6 ml) at room temperature for 90 minutes to give 1,2-dihydro-6,7-dihydroxy-2-methyl-1-oxo-isoquinoline-3-carboxylic acid; NMR (DMSO-d$_6$/CF$_3$COOD) 3.6(s, 3H); 7.03(s, 1H); 7.15(s, 1H); 7.6(s, 1H). |

We claim:

1. A cephalosporin compound the formula (IV)

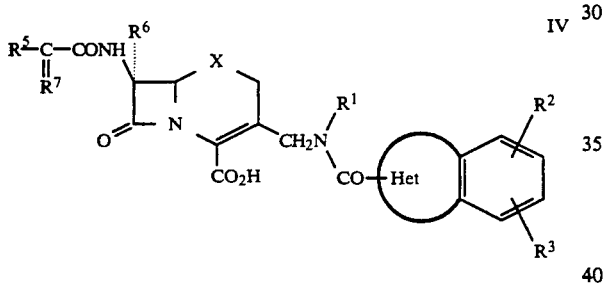

or salt or ester thereof wherein:

$R^1$ is hydrogen, $C_{1-6}$alkyl optionally substituted by halo, hydroxy, $C_{1-4}$alkoxy, carboxy, amino, cyano, $C_{1-6}$alkanoylamino, phenyl or heteroaryl, or $R^1$ is $C_{2-6}$alkenyl;

Het is a 5- or 6-membered heterocyclic ring selected from a group of the formulae II–III:

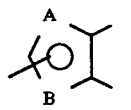

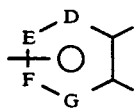

wherein A is CH or a nitrogen atom; B is oxygen, sulphur or a group $NR^4$; one or two of D, E, F and G are nitrogen atoms and the remainder are CH groups:

the ring Het being fused by any two adjacent carbon atoms to the benzene ring; and Het being bonded via a carbon atom to the —CH$_2$NR$^1$CO— group;

$R^2$ is hydroxy or an in vivo hydrolysable ester thereof;

$R^3$ is ortho to $R^2$ and is hydroxy or an in vivo hydrolysable ester thereof;

$R^4$ is hydrogen or hydroxy, or $C_{1-6}$alkoxy, phenoxy, $C_{2-6}$alkenyl or $C_{1-6}$alkyl, (any of these groups being optionally substituted by hydroxy, $C_{1-6}$alkoxy, cyano, amino, $C_{1-6}$alkylamino, di-$C_{1-6}$alkylamino, carboxy, $C_{1-6}$alkoxycarbonyl, $C_{1-6}$alkanoyloxy, carbamoyl, $C_{1-6}$alkylcarbamoyl, di-$C_{1-6}$alkylcarbamoyl, $C_{1-6}$alkoxycarbonylamino, phenyl, phenyl$C_{1-6}$alkyl, carboxyaminocarbonyl, $C_{1-6}$alkoxycarbonylaminocarbonyl, benzoyl or $C_{3-8}$cycloalkyl) or $R^4$ is phenyl, $C_{3-8}$ cycloalkyl, amino, $C_{1-6}$alkylamino or di-$C_{1-6}$alkylamino: wherein the fused Het-benzene ring system and/or any phenyl group is further optionally substituted by at least one substituent selected from $C_{1-6}$alkyl, halo, hydroxy, hydroxy $C_{1-6}$alkyl, cyano, trifluoromethyl, nitro, amino, $C_{1-6}$alkylamino, di-$C_{1-6}$alkylamino, phenyl $C_{1-6}$alkylamino, $C_{1-6}$alkanoyl, $C_{1-6}$alkoxy, $C_{1-6}$alkylthio, $C_{1-6}$alkanoyloxy, carbamoyl, $C_{1-6}$alkylcarbamoyl, di-$C_{1-6}$alkyl carbamoyl, carboxy, carboxy $C_{1-6}$alkyl, $C_{1-6}$alkoxycarbonyl$C_{1-6}$alkyl, sulpho, sulpho$C_{1-6}$alkyl, sulphonamido, $C_{1-6}$alkylsulphonamido, $C_{1-6}$alkoxycarbonyl, $C_{1-6}$alkanoylamino, thioureido and amidino;

X is sulphur or sulphinyl;

$R^6$ is hydrogen, methoxy or formamido; $R^5$ is 2-aminothiazol-4-yl or 2-aminooxazol-4-yl each optionally substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^7$ is of the formula $=N.O.R^8$ (having the syn configuration about the double bond) wherein $R^8$ is hydrogen, (1–6C)alkyl, (3–8C)cycloalkyl, (1–3C)alkyl(3–6C)cycloalkyl, (3–6)cycloalkyl(1–3C)alkyl, (3–6C)alkenyl optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di-(1–4C)alkylcarbamoyl(1–4C)alkyl, (1–4C)haloalkylcarbamoyl(1–4C)alkyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or R⁸ is of the formula V:

V wherein q is one or two and R⁹ and R¹⁰ are independently hydrogen or C₁₋₄alkyl; or R⁸ is of the formula VI:

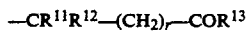

VI wherein r is 0-3, R¹¹ is hydrogen, (1-3C)alkyl or methylthio, R¹² is hydrogen (1-3C)alkyl, (3-7C)cycloalkyl, cyano, carboxy (2-5C)carboxyalkyl or methanesulphonylamino, or R¹¹ and R¹² are joined to form, together with the carbon to which they are attached, a (3-7C)carbocyclic ring, and R¹³ is hydroxy, amino, (1-4C)alkoxy, (1-4C) alkylamino or of the formula NHOR¹⁴ in which R¹⁴ is hydrogen or (1-4C)alkyl;

or R⁷ may be of the formula =CH.R¹⁵ wherein R¹⁵ is hydrogen, halogen, (1-6C)alkyl, (3-7C)cycloalkyl, (2-6C)alkenyl, (3-7C)cycloalkenyl, phenyl or benzyl.

2. A compound according to claim 1 wherein Het is quinoline, isoquinoline, quinazoline, quinoxaline, cinnoline, or phthalazine optionally substituted by R⁴ wherein R⁴ is hydrogen, hydroxy, C₁₋₄alkoxy, C₁₋₆alkyl, C₃₋₈cycloalkyl, hydroxyC₁₋₆alkyl, phenyl, phenylC₁₋₆alkyl, C₂₋₆alkenyl, aminoC₂₋₆alkyl, carbamoylC₁₋₆alkyl, C₁₋₆alkoxycarbonyl C₁₋₆alkyl or carboxyC₁₋₆alkyl:

and either ring of the Het-benzene ring system is optionally substituted by one or more atoms or groups selected from C₁₋₆alkyl, halo, hydroxy, hydroxyC₁₋₆alkyl, nitro, amino, C₁₋₆alkylamino, diC₁₋₆alkylamino phenylC₁₋₆alkylamino, C₁₋₆alkoxy, carboxyC₁₋₆alkyl, C₁₋₆alkanoylamino, trifluoromethyl, carboxy, carbamoyl, C₁₋₆alkylcarbamoyl, di-C₁₋₆alkylcarbamoyl, C₁₋₆alkanoyl, C₁₋₆alkylthio, cyano and C₁₋₆alkoxycarbonyl.

3. A compound according to claim 1 wherein R² and R³ are both hydroxy.

4. A compound according to claim 1 wherein the cephalosporin compound has a 3-position substituent of the sub-formula xiv):

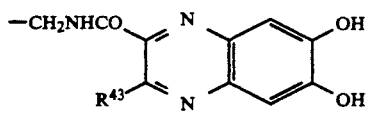

xiv)

wherein R⁴³ is hydrogen, chloro, bromo, carboxy, C₁₋₆alkoxycarbonyl, amino, C₁₋₆alkylamino or phenylC₁₋₆alkylamino.

5. A compound according to claim 1 wherein R⁵ is 2-aminothiazol-4-yl, R⁷ is a group =NOR⁸ wherein R⁸ is C₁₋₆alkyl, 1-carboxycyclobutyl, 1-carboxycyclopentyl or 2-carboxyprop-1-yl, R⁶ is hydrogen, X is sulphur and the 3-position substituent is of the sub-formula xiv)

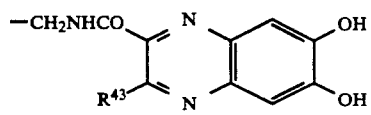

xiv)

wherein R⁴³ is hydrogen, chloro, bromo, carboxy, C₁₋₆alkoxycarbonyl, amino, C₁₋₆alkylamino or phenylC₁₋₆alkylamino.

6. A compound according to claim 5 wherein R⁸ is 2-carboxyprop-2-yl.

7. A compound according to claim 1 which is: quinoxalin-3-carboxamidomethyl)ceph-3-em-4-carboxylic acid.

8. A pharmaceutical composition which comprises a compound according to claim 1 and a pharmaceutically acceptable carrier.

* * * * *